(12) United States Patent
De Reuse et al.

(10) Patent No.: US 6,248,551 B1
(45) Date of Patent: Jun. 19, 2001

(54) HELICOBACTER ALIPHATIC AMIDASE AMIE POLYPEPTIDES, AND DNA SEQUENCES ENCODING THOSE POLYPEPTIDES

(75) Inventors: Hilde De Reuse; Stephane Skouloubris, both of Paris; Agnes Labigne, Burress/Yvette, all of (FR)

(73) Assignee: Institut Pasteur (FR)

( * ) Notice: Subject to any disclaimer, the term of this patent is extended or adjusted under 35 U.S.C. 154(b) by 0 days.

(21) Appl. No.: 09/027,900

(22) Filed: Feb. 23, 1998

Related U.S. Application Data

(60) Provisional application No. 60/041,745, filed on Mar. 28, 1997.

(51) Int. Cl.⁷ ........................................... A61K 39/02

(52) U.S. Cl. ................... 435/18; 530/344; 530/350; 435/6; 435/32; 435/228; 435/106; 514/2

(58) Field of Search ................... 435/106, 228, 435/32; 424/195.1, 73; 530/344; 504/43; 514/340, 398, 2; 549/6; 438/18

(56) References Cited

U.S. PATENT DOCUMENTS

| | | | |
|---|---|---|---|
| 4,562,292 | * 12/1985 | Hammock et al. | 568/43 |
| 4,880,737 | * 11/1989 | Kerkoffs et al. | 435/106 |
| 5,238,838 | * 8/1993 | Kula et al. | 435/228 |
| 5,250,660 | * 10/1993 | Shuman | 530/344 |
| 5,273,984 | * 12/1993 | Clitherow | 514/340 |
| 5,378,455 | * 1/1995 | Kealey et al. | 424/73 |
| 5,472,695 | * 12/1995 | Neeman et al. | 424/195.1 |
| 5,552,427 | * 9/1996 | Matsutani et al. | 514/398 |
| 5,560,912 | * 10/1996 | Neeman et al. | 424/195.1 |
| 5,804,549 | * 9/1998 | Blackburn et al. | 514/2 |
| 5,840,917 | * 11/1998 | Oi et al. | 549/6 |
| 5,843,460 | * 12/1998 | Labigne et al. | 424/234.1 |
| 5,942,409 | * 8/1999 | Sachs et al. | 435/32 |
| 5,986,051 | * 11/1999 | Labigne et al. | 530/350 |
| 6,027,878 | * 2/2000 | Labigne et al. | 435/6 |

FOREIGN PATENT DOCUMENTS

| | | |
|---|---|---|
| 0 272 026 | 6/1988 | (EP) . |
| 0 393 916 | 10/1990 | (EP) . |
| 835 928 | * 4/1996 | (EP) . |
| 90/04030 | * 4/1990 | (WO) . |
| WO 93/07273 | 4/1993 | (WO) . |
| 94/06474 | * 3/1994 | (WO) . |
| 94/09823 | * 5/1994 | (WO) . |
| WO 94/17190 | 8/1994 | (WO) . |
| WO 94/26901 | 11/1994 | (WO) . |
| 94/26901 | * 11/1994 | (WO) . |
| 95/22987 | * 8/1995 | (WO) . |
| WO 96/31235 | 10/1996 | (WO) . |
| WO 96/33732 | 10/1996 | (WO) . |
| 96/40893 | * 12/1996 | (WO) . |
| WO 97/06248 | 2/1997 | (WO) . |

OTHER PUBLICATIONS

Skouloubris et al., "Identification and Characterization Of An Aliphatic Amidase in *Helicobacter pylori*," *Mol. Microbiology*, 25 (5), pp. 989–998 (1997).

(List continued on next page.)

Primary Examiner—Lynette R. F. Smith
Assistant Examiner—Ginny Allen Portner
(74) Attorney, Agent, or Firm—Finnegan, Henderson, Farabow, Garrett & Dunner L.L.P.

(57) ABSTRACT

This invention relates to Helicobacter species aliphatic amidase AmiE polypeptides, the DNA encoding those polypeptides and transformed microorganisms capable of expressing those polypeptides. This invention also relates to the use of Helicobacter sp. (particularly *Helicobacter pylori*) amidase AmiE polypeptides and antibodies specific for those polypeptides in immunogenic, therapeutic, and diagnostic applications. The invention additionally relates to processes of producing Helicobacter species aliphatic amidase AmiE polypeptides and intermediates useful in the production of those polypeptides.

2 Claims, 23 Drawing Sheets

OTHER PUBLICATIONS

International Search Report.

Tomb et al, sequence allignment, Nature, Aug. 1997, vol. 388(6642), pp. 539–547, EMBL accession Nos. AE000548, AE00051, (abstract)1.*

Sienko et al, Chemistry:principles and properties, McGraw–Hill Book company, copy right 1966, p. 502, 1997.*

Hollaway et al (1980), Biochem. J. Dec. 1, 1980, vol. 1991(3), pp. 811–826, (abstract).*

Wilson et al (1995), J. Biol. Chem.. Aug. 11, 1995, vol. 270(32), pp. 18818–18824 (abstract).*

Nawaz et al (1994), Appl. Environ. Microbiol. Sep. 1994, vol. 60(9), pp. 3343–3348.*

Chebrou et al (1996), Gene, vol. 182, pp. 215–218, Dec. 1996.*

Sigma Catologue, (1987), Sigma Chemical Company, p. 500,col. 1, prod. No. D2141 or D0778.*

Stark et al (1997), Sep., Journal of Med. Microbiology, vol. 46(9), pp. 793–800.*

Ferrero et al (1994), Infect. Immun., Nov. 1994, vol. 62(11), pp. 4981–4989 (abstract).*

Stoschus et al (Aug. 1996), Eur. J. Gastroenterolog. Hepatol., vol. 8(8), p. 811–813.*

Nagata, K et al, Infection Immunity, Nov. 1992, vol. 60(11), pp. 4862–4631 (abstract).*

Stedman's Medical Dictionary, 26th Edition, 1995, Willaims & Wilkins, p. 58, col. 1–2.*

Tomb et al, Nature, vol. 388, Aug. 7, 1997, pp. 539–547.*

Gregoriou, M et al, Eur. J. Biochem., May 2, 1979, vol. 96(1), pp. 101–108 (abstract).*

Novo, C et al., FEBS Letters, Jul. 3, 1995, vol. 367(3), pp. 275–279, (abstract).*

Mobley, HL et al, Scand. J. Gastroenterol., vol. 187, 1991, pp. 39–46 (abstract).*

Slomiany, BL et al, Arzneimittelforschung, Apr. 1997, vol. 47(4A), pp. 475–482.*

Konturek, PC et al, Arzneimittelforschung, Apr. 1997, vol. 47(4a), pp. 578–589.*

Brown et al, 1987, J. Gen. Microbio. vol. 133, pp. 1527–1533.*

Cuenca et al, Gastroenterology, vol. 110(8), pp. 1770–1775, 1995.*

Eaton et al, Infection Immunity, Jul. 1991, vol. 59(7), pp. 2470–2475.*

Pappo et al, Infection Immunity, Apr. 1995, vol. 63(4) pp. 1246–1252.*

Corthesy–Theulaz et al, Gastroenterology, vol. 109, pp. 115–121, 1995.*

Davin et al, Gastroenterology, vol. 104(4), Apr. 1993, p. 127, abstract D182.*

* cited by examiner a) first internal peptide VWGVFSLTGEK   (SEQ. ID NO: 1)

oligonucleotide H36 :
5' GTiTGGGGiGTiTT(T/C)(A/T)(C/G)i(C/T)TiACiGG 3'   (SEQ. ID NO: 2)

b) second internal peptide   VSLIICDDGNYPEIW   (SEQ. ID NO: 3)

oligonucleotide H37 :
5' CCAiAT(C/T)TCiGG(A/G)TA(A/G)ATiCC(A/G)TC(A/G)TC(A/G)C 3' (SEQ. ID NO: 4)

c) non-degenerate   oligonucleotides oligonucleotide H46 :
5'-CCTTATAACACTTTGATTCTTGTC-3'   (SEQ. ID NO: 15)

oligonucleotide H49 :
5'-CAAGCCCTTAGGCCCATCAACC-3'   (SEQ. ID NO: 16)

Figure 1

```
         H36-->
         1                                                          60/20
(SEQ. ID NO: 5)  AAT CCT TAT AAC ACT TTG ATT CTT GTC AAT GAT AAG GGT GAG ATC GTG CAA AAA TAC CGC
(SEQ. ID NO: 6)  asn pro tyr asn thr leu ile leu val asn asp lys gly glu ile val gln lys tyr arg 120/40
AAA ATC TTG CCT TGG TGC CCT ATT GAA TGT TGG TAT CCT GGG GAT AAA ACT TAT GTG GTT
lys ile leu pro trp cys pro ile glu cys trp tyr pro gly asp lys thr tyr val val 147/49
GAT GGG CCT AAG GGC TTG AAA GTT TCT
asp gly pro lys gly leu lys val ser

Plasmid name: pILL400
Plasmid size: 8 000 bp

Comments: Insertion of the 2 600 bp *HindIII* fragment of cosmid IIIG5 (carrying the complete *amiE* gene) into the *HindIII* site of vector pILL570.

Plasmid name: pILL405
Plasmid size: 4 200 bp

Comments: Insertion of the 1 520 bp XhoI/BglII fragment from pILL400 (carrying the complete amiE gene) into the SalI/BamHI sites of vector pUC19.

Plasmid name: pILL417
Plasmid size: 3 900 bp

Comments: Insertion of the 1 230 bp *BstEII/EcoRI* fragment from plasmid pILL405 into the *SmaI/EcoRI* sites of vector pUC19.

Plasmid name: pILL835
Plasmid size: 5 400 bp

Comments: Replacement of the *PstI/SspI* fragment of vector pBR322 by the 1 570 bp *XhoI/PstI* fragment of pILL400.

Plasmid name: pILL836
Plasmid size: 6 900 bp

Comments: Insertion of the 1 500 kb *XmaI* fragment containing the gene conferring kanamycin resistance (from pILL200, unpublished) into the *XmaI* site, situated at 147 bp from the *amiE* start codon in pILL835.

(SEQ. ID NO: 7)

PILL405

TTGTGTGGAATTGTGAGCGGATAACAATTTCACACAGGAAACAGCTATGACCATGATTACGCCAAGCTTGCATGCCTGC
AGGTCGAGCGCTCATTAAAAAAGGCGTTGTTTTTGATGAAATCTTTTATAACCAGGATTTGGAACTCACTGAGGGCGCT
AGGAGCAATCTTGTTTTAGAAATCCATAACAGGCTTTTAACCCCTTATTTTAGCGCGGGCGCGTTAAACGGGACGGGTG
TTGTGGGGTTGTTAAAAAAAGGGTCTTGTTGGGCATGCCCTTTGAAATTGCAAGACTTGCAAAGAGCGGCTAAAATCTA
TTGCATTAACGCGCTATATGGCTTAGTGGAAGTGAAAATCAAATAACCATAAAAATAGAGCAACTAAAACCTCATTTTT
AGAAATAGGTTACCCAATGGAGCAAAAAAGTTAAAACTCGCCCATAATAATCATAATGATTAAAGTTTTTATATTCATT
ATAGATCCATTTACACAATTATTTTATAAATCCAAATAGAGGGTTTGTAGGAACTCTCATCAAAAAATAAGGAACATAA
TATGAGACATGGAGATATTAGTAGCAGCCCAGATACTGTGGGTGTAGCGGTAGTTAATTATAAGATGCCTAGACTCCAC
ACTAAAGAACAAGTGTTGGAAAATTGTCGCAATATCGCTAAGGTGATTGGTGGGGTCAAACAGGGTTTGCCCGGGTTGG
ATCTGATTATTTTCCCTGAATACAGCACGCATGGGATCATGTATGACAGACAAGAAATGTTTGACACAGCCGCAAGCGT
TCCTGGAGAAGAAACTGCGATCTTTGCTGAGGCTTGTAAGAAAAACAAGGTTTGGGGAGTGTTCTCTTTGACTGGGGAA
AAACACGAGCAAGCCAAAAAGAATCCTTATAACACTTTGATTCTTGTCAATGATAAGGGTGAGATCGTGCAAAAATACC
GCAAAATCTTGCCTTGGTGCCCTATTGAATGTTGGTATCCTGGGGATAAAACTTATGTGGTTGATGGGCCTAAGGGCTT
GAAAGTTTCTTTGATCATTTGCGATGATGGGAACTACCCTGAAATTTGGCGCGATTGCGCGATGCGTGGGGCACAACTC
ATTGTGCGCTGTCAAGGTTACATGTATCCGGCTAAGGAGCAACAAATTGCGATCGTGAAAGCTATGGCGTGGGCCAATC
AATGTTATGTAGCGGTAGCGAATGCGACCGGTTTTGATGGGGTGTATTCCTATTTTGGGCATTCTAGCATTATTGGTTT
TGATGGGCATACTTTGGGCGAATGCGGGGAAGAAGAAATGGTCTTCAATACGCTCAACTTTCCGTGCAACAAATCCGT
GATGCAGAAAATACGACCAAAGCCAAAACCAACTCTTCAAACTCTTGCACAGAGGTTATAGTGGGGTTTTTGCTAGTG
GCGATGGGGATAAGGGTGTGGCGGAATGCCCTTTTGAGTTCTATAAAACTTGGGTTAATGACCCAAAAAAAGCTCAAGA
AAATGTAGAAAAAATCACTCGCCCAAGCGTGGGTGTGGACGCTTGTCCTGTGGGCGATTTGCCCACGAAATAAAGGGCA
AAAGGAGGGGGGGCTTCATAGAAGCTTCTAGAGATCCCCGGGTACCGAGCTCGAATTCACTGGCCGTCGTTTTACAACG
TCGTGACTGGGAAAAC

Figure 4(a)

(SEQ ID NO: 8)

```
                                                    ScrF I                HinP I
    HinP I                                          PflM I                Hha I
    Hha I                                           EcoR II               Hae II
    Hae II              Mnl I                       BstN I     Dde I      Mae I
Taq I Eco47 III Mse I                                                             
    ▼ ▬    ▼                  ▼                       ▼▬      ▬  ▼▬  ▼
GGTCGAGCGCTCATTAAAAAGGCGTGTTTTGATGAAATCTTTATAACCAGGATTTGAACTTCACTGAGGGCGCTAG  160
CCAGCTCGCGAGTAATTTTTCCGCACAAAACTACTTTAGAAATATTGGTCCTAAACCTTGAAGTGACTCCCGCGATC
   83    86  94                                     131                148  157
         86  87                                     131                150
                                                    131                153
                                                    131                154
```

```
                                          HinP I  Mse I
                                    BstU I Hha I  BstU I
               Mse I                   ▼▬▼    ▼▬ ▼
GAGCAATCTTGTTTAGAAATCCATAAACAGGCTTTAACCCCTTATTTTAGCGGGCGCGTTAAACGGGACGGGTGTTG  240
CTCGTTAGAACAAATCTTTAGGTATTGTCCGAAATTGGGGAATAAAATCGCCCGCGCAATTTGCCCTGCCCACAAC
     ▼                              ▼             ▼▼▼    ▼▼ ▼
                                   195           211   218
                                                 211   222
                                                 212
                                                 217
```

FIG. 4b-I

```
                                  Nla III
                                  Sph I
                                  NspH I
                   Mse I          Nsp7524 I                        Fnu4H I
                   |              ||                               |
TGGGGTTGTTAAAAAGGGTCTTGTTGGGCATGCCCCTTTGAAATTGCAAGACTTGCAAAGAGCGGCTAAAATCTATTGC  320
ACCCCAACAATTTTTCCCAGAACAACCCGTACGGGGAAACTTTAACGTTCTGAACGTTTCTCGCCGATTTTAGATAACG
   |            ▼              |▼             ▼         ▼      ▼         ▼
   249                         269                                       303
                               270

HinP I
     Hha I
     BstU I           Dde I                                Mnl I
Mse I ||              |                                   |
ATTAACGCGCTATATGGCTAGTGGAAGTGAAATGAAACTAAAATAGAGCAACTAAAACCTCATTTTTAGAAA  400
TAATTGCGCGATATACCGATCACCTTCACTTTACTTTGATTTTATCTCGTTGATTTTGGAGTAAAAATCTTT
|   ||              |                                   ▼         ▼          ▼
322                 338                                            386
326
```

FIG. 4b-2

```
                                                                              Mme I
                                                                              ScrF I
                                                                              Nci I
                                                                              Msp I
                                                                              Hpa II
                                                                              Bcn I
                                                                              Xma I
                                                                              Sma I
                                                                              Sec I    Sau3A I
                                                                              ScrF I   Mbo I
                                                                              Nci I    Dpn I
                                                                              Bcn I    BstY I
                                      Hph I              Tth111 II            Ava I    Alw I
               Mme I         Dde I     |                    |                  | ||     ||
                |              |       |                    |                  | ||     ||
ACAAGTGTTGGAAAATTGTCGCAATATCGCTAAGGTGATTGGTGGGTCAAACAGGGTTTGCCCGGGTTGGATCTGATTA
TGTTCACAACCTTTTAACAGCGTTATAGCGATTCCACTAACCACCCCAGTTTGTCCCAAACGGGCCCAACCTAGACTAAT
 |Y                          Y                             |Y       Y||       Y
 647                         670                           689      702       710   720

Full restriction map of the *H. pylori* insert of plasmid pILL405.

Sequence of the *H. pylori amiE* gene and deduced amino acid sequence of the AmiE protein.
Positions of hybridization with the two degenerated oligonucleotides H36 and H37 are indicated.

```
               1/1                                          31/11
(SEQ ID NO: 9) ATG AGA CAT GGA GAT ATT AGT AGC AGC CCA GAT ACT GTG GGT GTA GCG GTA GTT AAT TAT
(SEQ ID NO:10)  M   R   H   G   D   I   S   S   S   P   D   T   V   G   V   A   V   V   N   Y

61/21                                        91/31
               AAG ATG CCT AGA CTC CAC ACT AAA GAA CAA GTG TTG GAA AAT TGT CGC AAT ATC GCT AAG
                K   M   P   R   L   H   T   K   E   Q   V   L   E   N   C   R   N   I   A   K

121/41                                       151/51
               GTG ATT GGT GGG GTC AAA CAG GGT TTG CCC GGG TTG GAT CTG ATT ATT TTC CCT GAA TAC
                V   I   G   G   V   K   Q   G   L   P   G   L   D   L   I   I   F   P   E   Y

181/61                                       211/71
               AGC ACG CAT GGG ATC ATG TAT GAC AGA CAA GAA ATG TTT GAC ACA GCC GCA AGC GTT CCT
                S   T   H   G   I   M   Y   D   R   Q   E   M   F   D   T   A   A   S   V   P

241/81                        271/91                          5'----------
               GGA GAA GAA ACT GCG ATC TTT GCT GAG GCT TGT AAG AAA AAC AAG GTT TGG GGA GTG TTC
                G   E   E   T   A   I   F   A   E   A   C   K   K   N   K   V   W   G   V   F
```

FIG. 5a

```
301/101
         -------> 3' H36
         TCT TTG ACT GGG GAA AAA CAC GAG CAA GCC AAA AAG AAT CCT TAT AAC ACT TTG ATT CTT
          S   L   T   G   E   K   H   E   Q   A   K   K   N   P   Y   N   T   L   I   L

331/111

361/121
         GTC AAT GAT AAG GGT GAG ATC GTG CAA AAA TAC CGC AAA ATC TTG CCT TGG TGC CCT ATT
          V   N   D   K   G   E   I   V   Q   K   Y   R   K   I   L   P   W   C   P   I

391/131

421/141
         GAA TGT TGG TAT CCT GGG GAT AAA ACT TAT GTG GTT GAT GGG CCT AAG GGC TTG AAA GTT
          E   C   W   Y   P   G   D   K   T   Y   V   V   D   G   P   K   G   L   K   V

451/151

481/161
              3' <------------------------- 5' H37
         TCT TTG ATC ATT TGC GAT GAT GGG AAC TAC CCT GAA ATT TGG CGC GAT TGC GCG ATG CGT
          S   L   I   I   C   D   D   G   N   Y   P   E   I   W   R   D   C   A   M   R

511/171

541/181
         GGG GCA GAA CTC ATT GTG CGC TGT CAA GGT TAC ATG TAT CCG GCT AAG GAG CAA CAA ATT
          G   A   E   L   I   V   R   C   Q   G   Y   M   Y   P   A   K   E   Q   Q   I

571/191

601/201
         GCG ATC GTG AAA GCT ATG GCG TGG GCC AAT CAA TGT TAT GTA GCG AAT GCG ACC
          A   I   V   K   A   M   A   W   A   N   Q   C   Y   V   A   N   A   T

```
661/221
GGT TTT GAT GGG GTG TAT TCC TAT TTT GGG CAT TCT AGC ATT ATT GGT TTT GAT GGG CAT
 G   F   D   G   V   Y   S   Y   F   G   H   S   S   I   I   G   F   D   G   H

721/241                                               691/231
ACT TTG GGC GAA TGC GGG GAA GAA AAT GGT CTT CAA TAC GCT CAA CTT TCC GTG CAA
 T   L   G   E   C   G   E   E   N   G   L   Q   Y   A   Q   L   S   V   Q

781/261                                               751/251
CAA ATC CGT GAT GCG AGA AAA TAC GAC CAA AGC CAA AAC CAA CTC TTC AAA CTC TTG CAC
 Q   I   R   D   A   R   K   Y   D   Q   S   Q   N   Q   L   F   K   L   L   H

841/281                                               811/271
AGA GGT TAT AGT GGG GTT TTT GCT AGT GGC GAT GGG GAT AAG GGT GTG GCG GAA TGC CCT
 R   G   Y   S   G   V   F   A   S   G   D   G   D   K   G   V   A   E   C   P

901/301                                               871/291
TTT GAG TTC TAT AAA ACT TGG GTT AAT GAC CCC AAA AAA GCT CAA GAA AAT GTA GAA AAA
 F   E   F   Y   K   T   W   V   N   D   P   K   K   A   Q   E   N   V   E   K

961/321                                               931/311
ATC ACT CGC CCA AGC GTG GGT GTG GAC GCT TGT CCT GTG GGC GAT TTG CCC ACG AAA TAA
 I   T   R   P   S   V   G   V   D   A   C   P   V   G   D   L   P   T   K   *
                                                      991/331
```

FIG. 5c

Comparison of the aminoacid sequence of the AmiE amidase of *Helicobacter pylori* (AmiE-HP) with the two available amidase sequences from (i) *Rhodococcus* sp. R312 (also designated *Brevibacterium* sp. R312, AmiE-Brevi) and from *Pseudomonas aeruginosa* (AmiE-Pseudo).

```
                    1                                                      50
AmiE-HP    MRHGDISSSP DTVGAVVNY KMPRLHTKEQ VLENCRNIAK VIGGVKQGLP  (SEQ ID NO: 10)
AmiE-Brevi *********N ********** *****DRAG  ***A*K**D MMI*M*T***  (SEQ ID NO: 11)
AmiE-Pseudo ********N ********** *****AAE  ***D*A*K**D M*V*M*****  (SEQ ID NO: 12)

51                                                     100
AmiE-HP    GLDLIIFPEY STHGIMYDRQ EMFDTAASVP GEETAIFAEA CKKNKVWGVF
AmiE-Brevi *MVV Q*NEE  YA***TI* *D***SA*  *READT****
AmiE-Pseudo *MVV LQ***PA ME***VAI* **ESR* *R*AN*****

101                                                    150
AmiE-HP    SLTGEKHE.Q AKKNPYNTLI LVNDKGEIVQ KYRKILPWCP IECWYPGDKT
AmiE-Brevi *I*QDH PN*P****** *IDN**** R***** G*****T*
AmiE-Pseudo **REH  PR*A****** *IDRN*** ******I G****GQ*

151                                                    200
AmiE-HP    YVVDGPKGLK VSLIICDDGN YPEIWRDCAM RGAELIVRCQ GYMYPAKEQQ
AmiE-Brevi TE** I***** ****** K***** ****D
AmiE-Pseudo SE**M* I******* ****** K***** ****D

201                                                    250
AmiE-HP    IAIVKAMAWA NQCYVAVANA TGFDGVYSYF GHSSIIGFDG HTLGECGEEE
AmiE-Brevi VMMS****** *N******* *A********* ****A****** R****T****
AmiE-Pseudo VMMA****** *N******* *A********* ****A****** R*********

251                                                    300
AmiE-HP    NGLQYAQLSV QQIRDARKYD QSQNQLFKLL HRGYSGVFAS GDGDKGVAEC
AmiE-Brevi Y*I******* SA****** *EN* ****HI*** ******** **H*A ********D*
AmiE-Pseudo M*I***** L S**** *AN* **H**I* ****LQ **RL***

301                                                    346
AmiE-HP    PFEFYKTWVN DPKKAQENVE KITRPSVGVD ACPVGDLPTK Z......
AmiE-Brevi ****LT *AQ**R A*DT*A D*RNVE KTVEA.
AmiE-Pseudo ***R**T *AERD* RLSTTA Q**RYE GLEKEA
```

FIG. 6

```
1/1                                              31/11
ATG CCT GCA GGT CGA GCG CTC ATT AAA AAA GGC GTT TTT GAT GAA ATC TTT TAT AAC  (SEQ ID NO: 13)
 M   P   A   G   R   A   L   I   K   K   G   V   F   D   E   I   F   Y   N   (SEQ ID NO: 14)

61/21                                            91/31
CAG GAT TTG GAA CTC ACT GAG GGC GCT AGG AGC AAT CTT GTT TTA GAA ATC CAT AAC AGG
 Q   D   L   E   L   T   E   G   A   R   S   N   L   V   L   E   I   H   N   R

121/41                                           151/51
CTT TTA ACC CCT TAT TTT AGC GCG GGC GCG TTA AAC GGG ACG GGT GTT GTG GGG TTG TTA
 L   L   T   P   Y   F   S   A   G   A   L   N   G   T   G   V   V   G   L   L

181/61                                           211/71
AAA AAG GGT CTT GTT GGG CAT GCC CCT TTG AAA TTG CAA GAC TTG CAA AGA GCG GCT AAA
 K   K   G   L   V   G   H   A   P   L   K   L   Q   D   L   Q   R   A   A   K

241/81                                           271/91
ATC TAT TGC ATT AAC GCG CTA TAT GGC TTA GTG GAA GTG AAA ATC AAA TAA
 I   Y   C   I   N   A   L   Y   G   L   V   E   V   K   I   K   *
```

Truncated ORF situated upstream from the *amiE* gene on plasmid pILL405, this ORF corresponds to the 3'-extremity of a gene of unknown function.

FIG. 7

HELICOBACTER ALIPHATIC AMIDASE AMIE POLYPEPTIDES, AND DNA SEQUENCES ENCODING THOSE POLYPEPTIDES

This application claims the benefit under 35 U.S.C. §119(e) of U.S. Provisional Application No. 60/041,745, filed Mar. 28, 1997.

This invention relates to Helicobacter species aliphatic amidase AmiE polypeptides, the DNA encoding those polypeptides, and transformed microorganisms capable of expressing those polypeptides. In addition, this invention relates to the use of Helicobacter sp. particularly *Helicobacter pylori*) amidase AmiE polypeptides and antibodies specific for those polypeptides in immunogenic, therapeutic and diagnostic application.

BACKGROUND OF THE INVENTION

An aliphatic amidase is an acylamide amidohydrolase (E.C. 3.5.1.4) (Merck Index). It hydrolyses short-chain aliphatic amides (C1–C4 such as acrylamide, acetamide, propionamide or isobutyramide) to produce ammonia and the corresponding organic acid. In addition, an aliphatic amidase possesses acyl transferase activity, i.e., it is able to transfer the acyl group of amides to hydroxylamine to form an acyl hydroxamate plus ammonia.

Aliphatic amidases have been identified in *Pseudomonas aeruginosa* (Brammar et al., 1987) and Rhodococcus sp. R312 (previously named Brevibacterium sp. R312; Soubrier et al., 1992). Other aliphatic amidases have been identified in *Methylophilus methylotrophus* (Silman et al., 1991), Arthrobacter sp. J-1 (Asano et al., 1982), and *Alcaligenes eutrophus* (Friedrich and Mitrenga, 1981). However, no molecular characterization of these latter three enzymes has been reported.

Aliphatic amidases are cytoplasmic enzymes; they have very similar enzymatic properties and molecular masses (38.4 kDa for *P. aeruginosa;* 38.2 kDa for Rhodococcus sp. R312; 37.8 kDa for *M. methylotrophus;* and 39 kDa for Arthrobacter sp. J-1), and have either a tetra-, hexa-, or octameric structure. Some of these amidases have been shown to be inducible by their amide substrate. Database searches with the amino acid sequences of these aliphatic amidases indicates that they are more closely related to nitrilases (which catalyze the direct cleavage of nitrites to ammonia and to the corresponding acid) than to the nitrile hydratases (which hydrolyze nitrites to produce amides) or amidases from other classes (Novo et al., 1995).

The prevailing theory on the physiological role of the aliphatic amidases is that hydrolysis of amides supplies carbon and nitrogen sources to the bacteria. Curiously, Helicobacter sp. possess a very potent urease, which should be sufficient for nitrogen supply in this genus of bacteria. However, Helicobacter sp. are not the only bacteria possessing both urease and amidase, since this is also the case for *P. aeruginosa, M. methylotrophus,* and *A. eutrophus.*

Acrylamide, an aliphatic amide, is extensively used in a great number of industrial processes. Global production of acrylamide has been estimated to be over 200,000 tons. Widespread use and indiscriminate discharge of acrylamide have resulted in the contamination of terrestrial and aquatic ecosystems throughout the world. Other aliphatic amides are either active ingredients or metabolites of herbicide degradation (Roberts, 1984). Elimination of acrylamide and other toxic aliphatic amide by-products by an aliphatic amidase would be of great importance because these substances pose serious health hazards for humans and animals (Nawaz et al., 1994, 1996) (Nagasawa and Yamada, 1989).

*Helicobacter pylori* has become identified as a primary cause of chronic gastroduodenal disorders, such as gastritis, dyspepsia, and peptic ulcers, in humans. *H. pylori* can be successfully eradicated (80% to 90%) by a treatment combining two antibiotics with a proton pump inhibitor. However, few antibiotics are active against *H. pylori,* and antibiotic resistant strains (e.g., to metronidazole or clarythromycin) have begun to appear. Like *H. pylori, Helicobacter heilmanii* has been identified as the cause of gastric ulcers in pigs. Porcine gastric ulcers lead to lower weight pigs and consequently, less food product production. Due to the presence of numerous urea positive bacteria in the porcine gastrointestinal tract, methods that are not based on urease are preferred for detecting, treating or preventing Helicobacter infections in pigs.

Thus, a need exists for an effective method of diagnosing, preventing, and treating gastrointestinal disorders caused by Helicobacter sp., particularly *H. pylori* and *H. heilmanii.*

SUMMARY OF THE INVENTION

This invention provides polynucleotides corresponding to Helicobacter species aliphatic amidase amiE. More particularly, this invention provides polynucleotides selected from the group consisting of:

(a) all or part of the DNA sequence encoding Helicobacter sp. and particularly, *Helicobacter pylori* aliphatic amidase amiE (depicted in FIG. 5);

(b) all or part of the DNA sequence depicted in FIG. 4;

(c) a DNA sequence which hybridizes with all or part of DNA sequence (a) or (b) under stringent conditions and encodes a polypeptide having the biological or immunological properties of Helicobacter sp. and particularly, *Helicobacter pylori* aliphatic amidase or a fragment thereof; and (d) an analog of DNA sequence (a), (b), or (c) resulting from the degeneracy of the genetic code.

Other aspects of this invention include polypeptides encoded by the polynucleotides of this invention; antibodies to those polypeptides; immunogenic, pharmaceutical, and therapeutic compositions comprising the polypeptides and antibodies of the invention; methods of using the polypeptides and antibodies of the invention to detect, treat or prevent Helicobacter sp. infections in man and animals; detection kits comprising the polypeptides and antibodies of the invention; processes for producing polypeptides according to the invention and intermediates useful in their production.

BRIEF DESCRIPTION OF THE DRAWINGS

FIGS. 1a and 1b depict N-terminal amino acid sequences of two internal peptides from an *H. pylori* protein with an apparent molecular mass of 49 kDa that has subsequently been identified as an aliphatic amidase. The sequences of degenerate oligonucleotides, H36 and H37, deduced from the two internal peptides are indicated under each amino acid sequence. H37 corresponds to the deduced anti-parallel sequence. Two residues at the same position in the H36 and H37 sequences (depicted as N/N) indicate that the oligonucleotide preparation contains a mixture of the two types of molecules. ("i" corresponds to inosine residues introduced in the degenerated oligonucleotides.) FIG. 1c identifies two primers, H46 and H49, used to amplify an internal sequence of the *H. pylori* amidase gene.

FIG. 2 depicts the sequence of the PCR product obtained with oligonucleotides H36 and H37 from chromosomic DNA of *H. pylori* strain 85P. This sequence corresponds to an internal sequence of the amiE gene of *H. pylori*. The numbers above the sequences correspond to the nucleic acid number/the amino acid number.

FIGS. 4a and 4b depict the sequence and full restriction map of the *H. pylori* DNA insert of plasmid pILL405, respectively.

FIG. 5 depicts the sequence of the *H. pylori* amiE gene and deduced amino acid sequence of the AmiE protein. Positions of hybridization with the two degenerate oligonucleotides H36 and H37 and of the two non-degenerate primers H46 and H49 are indicated. The predicted active site of the AmiE protein is underlined (residues 155 to 200) and the predicted active site nucleophile cys$^{166}$ residue is highlighted.

FIG. 6 provides a comparison of the amino acid sequence of the AmiE amidase of Helicobacter pylori (amidE-HP) with the two available amidase sequences from (i) Rhodococcus sp. R312 (also designated Brevibacterium sp. R312, amiE-Brevi) and from *Pseudomonas aeruginosa* (amiE-Pseudo).

FIG. 7 depicts a truncated open reading frame situated upstream from the amiE gene of *H. pylori*.

DESCRIPTION OF THE INVENTION

Figure 3A:
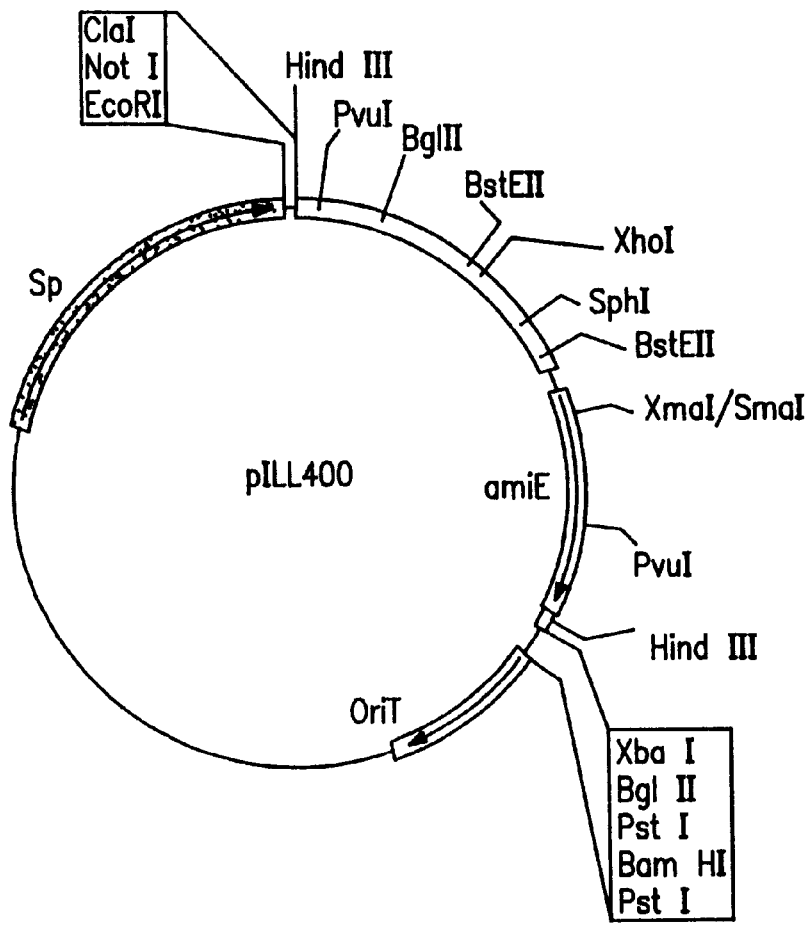
FIGS. 3a–3e depict restriction maps of plasmids pILL400, pILL405, pILL417, pILL835, and pILL836, respectively. The genes are indicated by boxes with an arrow showing the direction of their transcription. Sp, Ap, Km, and Tet correspond to the genes conferring resistance to spectinomycin, ampicillin, kanamycin, and tetracycline, respectively. Ori indicates the origin of replication and OriT the origin of transfer of a conjugative plasmid. lacZ corresponds to the gene coding for β-galactosidase, Plac to the lac promoter, and amiE to the gene coding for the *H. pylori* amidase.

We have identified an aliphatic amidase amiE gene of Helicobacter species. The amino acid sequence of the Helicobacter aliphatic amidase enzyme is closely analogous (75% identical residues) to the aliphatic amidases from *Pseudomonas aeruginosa* and Rhodococcus sp. R312. The *H. pylori* amiE DNA sequence shares 65% identity with *P. aeruginosa* and Rhodococcus sp. R312 amidase genes. (There is 81% identity between the *P. aeruginosae* and Rhodococcus sp. R312 amidase amino acid sequences and 79% identity between their respective nucleotide sequences.)

The invention includes purified polynucleotides encoding the aliphatic amidase of Helicobacter sp. and biologically equivalent variants of Helicobacter sp. aliphatic amidase AmiE, to expression vectors containing these polynucleotides, and to products genetically or immunologically related to Helicobacter sp. aliphatic amidase AmiE. The term "products genetically or immunologically related to Helicobacter sp. aliphatic amidase amiE" refers to the various products derived from original Helicobacter sp. aliphatic amidase amiE DNA whether they be corresponding RNAs, recombinant DNAs containing all or part of the original DNA, DNAs that, as a result of the degeneracy of the genetic code, encode the same polypeptide or fragments thereof as Helicobacter sp. aliphatic amidase amiE DNA, or DNAs capable of hybridizing with all or part of the Helicobacter sp. aliphatic amidase amiE DNA or other DNAs of this invention under stringent conditions (as defined by Southern, 1975), as well as the "immunological" products resulting from the expression of these DNAs, in competent cell hosts. Thus, the invention includes polypeptides resulting from the transcription and translation of all or part of the different open reading frames of original, recombinant or degenerated Helicobacter sp. aliphatic amidase amiE DNA or DNA capable of hybridizing with all or part of any of those DNAs under stringent conditions and antibodies against those polypeptides.

Antibodies according to this invention may be monoclonal or polyclonal and are specific for an isolated or purified Helicobacter sp. aliphatic amidase AmiE antigen or antigenic preparation comprising an isolated or purified Helicobacter sp. aliphatic amidase AmiE antigen. Such antibodies may be produced by methods well known in the art. The antibodies of this invention may be administered in an immunologically effective amount directly to a patient to confer passive immunity against Helicobacter sp. infection or to treat an existing infection. The term "immunologically effective amount" refers to the amount required to produce, either in a single dose or a series of doses, effective treatment or prevention of Helicobacter sp. infection in man or animals.

The purified or isolated DNAs, polypeptides and antibodies of this invention may be used in diagnostic kits and procedures to detect the presence of Helicobacter or Helicobacter antibodies in a sample from an infected patient or animal. Such diagnostic kits and procedures fall within the ambit of this invention. (The term "purified or isolated" means that the DNAs, polypeptides or antibodies are substantially free (more than 75%) from other products with which those DNAs, polypeptides or antibodies are normally found associated in nature.) For example, one embodiment of this invention uses a pair of primers (FIG. 1c) which specifically amplify (by PCR) internal sequences of the *H. pylori* amiE gene (FIG. 5) and thus, allow the detection of the bacteria directly on a biological specimen, such as gastric juice, biopsies, stools, or saliva. Another diagnostic procedure according to this invention is the use of aliphatic amidase as a marker to identify Helicobacter sp. in a sample. Only a limited number of markers are available, including urease, oxidase, catalase, alkaline phosphatase, and gamma-glutamyl transpeptidase activities. Increasing the number of markers will improve the specificity of Helicobacter sp. detection. Furthermore, because Helicobacter sp. is the only known gastrointestinal bacteria to produce aliphatic amidase, a quick and specific amidase biochemical assay can be developed to detect and identify Helicobacter sp. infection. One suitable assay uses acrylamide as a substrate and a colorimetric indicator, such as phenol red, which changes color as a consequence of pH modification.. If aliphatic amidase is present in a test sample, it hydrolyzes the acrylamide to ammonia causing a change in pH, and consequently, color.

Additional diagnostic embodiments of this invention include the use of isolated or purified amiE antigenic polypeptide, alone or in combination with other known Helicobacter antigen preparations, for serological diagnosis of Helicobacter infection, e.g., *H. pylori* infection in humans or *H. heilmanii* in pigs. Such diagnostic immunoassays are well known in the art, and include radioimmunoassays (RIA) and enzyme-linked immunosorbent assays (ELISA).

The invention further relates to the use of the DNA and encoded polypeptides of this invention for immunization and therapeutic purposes. Protocols for the use of isolated polynucleotides to provide an immune response upon in vivo translation of the polynucleotide are described, for example, in WO 90/11092 (Felgner et al.), incorporated herein by reference.

In one embodiment of this invention, isolated native or recombinant AmiE polypeptides or antigenic fragments may be administered to patients suffering from Helicobacter infection or to protect patients from contracting the infection. Prophylactic as well as therapeutic effects of the polypeptides of this invention may be assessed in the *H. felis*/mouse model or the *H. pylori*/mouse model using protocols previously described for UreB, and HspA (Ferrero et al., 1995). The immunogenic/therapeutic composition may comprise amidase polypeptides or antigenic fragments alone or in association with a mucosal adjuvant, such as cholera toxin, and/or previously described protective antigens, e.g., UreB and HspA.

As already noted, among the bacteria that colonize the gastrointestinal tract, Helicobacter sp. are the only bacteria known to express an aliphatic amidase. Therefore, using this amidase as a target to eliminate Helicobacter sp. (e.g., by administering a drug or other substance capable of inhibiting amidase activity) will result in a highly specific antibacterial effect. This Helicobacter sp. specific effect is achieved in one aspect of this invention by providing culture conditions where the aliphatic amidase activity becomes an essential function for Helicobacter sp. growth (or the growth of any other organism expressing the Helicobacter amiE gene) making it possible to select substances in vitro, which inhibit the amidase activity and thus, are toxic specifically to Helicobacter sp. An example of such culture conditions includes nitrogen starvation with amides as the only nitrogen source.

Another means to achieve a Helicobacter specific effect is to select a non-toxic substance that produces, when hydrolyzed by the aliphatic amidase, a product toxic to Helicobacter growth. For example, glycollamide has been shown to be highly toxic for in vitro bacterial growth when degraded in glycollate by an aliphatic amidase (Brown and Tata, 1987).

Analysis of the amidase catalytic properties (eventual involvement of a metal ion) and determination of the active site is of course of great importance for the design of Helicobacter sp. inhibitors. By analogy with nitrilases (Novo et al., 1995), a region from residue 155 to 200 (FIG. 5) containing a cysteine residue cys[166] is proposed to correspond to the *H. pylori* active site. Point mutations in the *P. aeruginosa* amidase have been shown to be sufficient to change its substrate specificity significantly (Clarke, 1984). These same techniques, applied to Helicobacter amidase, can be used to unequivocally identify the active site of that enzyme.

Another embodiment of this invention involves the use of Helicobacter aliphatic amidase polypeptides and/or recombinant microorganisms capable of overexpressing these polypeptides to eliminate toxic amides from a contaminated environment. In particular, these polypeptides or recombinant microorganisms may be used to degrade and detoxify acrylamide, which appears to be the best substrate of the Helicobacter aliphatic amidase. Methods of constructing microorganisms capable of overproducing selected polypeptides are well known in the art. One suitable method is described in Example 2.7 infra.

The practice of this invention employs conventional techniques of molecular biology, microbiology, and immunology, which are within the skill of the art. These techniques are fully described in the literature. These conventional techniques can be used to to prepare the polypeptides of this invention. Thus, this invention includes a process of preparing purified or isolated polypeptides according to this invention by culturing under suitable conditions a procaryotic or eucaryotic host cell transformed or transfected with a polynucleotide of this invention in a manner allowing the host cell to express the desired polypeptide and isolating the polypeptide expression product.

Other information, which may be useful in the practice of this invention, is fully described in WO 94/26901 (Labigne, et al.), incorporated herein by reference.

EXAMPLES 1.1 Bacterial Strains and Growth Conditions

*E. coli* MC 1061 (Casadaban and Cohen, 1980) cells were grown routinely at 37° C. on solid or liquid luria medium (Miller, 1992). *H. pylori* strains (N6 and 85P) were grown on a horse blood agar medium containing an antibiotic mixture and incubated under microaerobic conditions at 37° C. (Ferrero et al., 1992). The *H. pylori* N6-836 mutant strain was grown on the same supplemented medium with kanamycin (20 µg/ml). Antibiotic concentrations for the selection of recombinant *E. coli* were as follows: spectinomycin (40 µg/ml), ampicillin (100 µg/ml), kanamycin (50 µg/ml) and tetracyclin (20 µg/ml).

1.2 Microsequencing

Determination of the N-terminal amino acid sequence of two of the peptides generated by enzymatic proteolysis of a protein with an apparent molecular mass of 49 kDa was performed in the "Laboratoire de Microséquençage des Protéines" at the Institute Pasteur on an Applied Biosystems 473A Sequencer.

1.3 General Molecular Biology Techniques and Electroporation

Standard procedures for endonuclease digestions, ligation, agarose gel electrophoresis and elution of DNA fragments from agarose gels were used (Sambrook et al., 1989). *E. coli* strains were made competent and transformed with the standard $CaCl_2$ method (Sambrook et al., 1989). Small-scale plasmid preparations were prepared by the alkaline lysis procedure. Preparation of the cosmid or large-scale plasmid preparation was performed with the MAXI and MIDI qiagen columns (QIAGEN), respectively. Approx. 10 µg of plasmid pILL836 of a MAXI qiagen preparation were concentrated by ethanol precipitation without added salts and the pellet was dissolved into 2 µl of bidistillated water. This DNA preparation was used directly for electroporation. Strain N6 was used as a recipient strain for the electroporation experiments performed as described in Ferrero et al. (1992).

1.4 PCR Conditions and Direct Sequencing of PCR Products

The templates were approximately 10 ng, either from a chromosomic DNA preparation of strain N6 or 85P, or from different plasmid preparations. In order to prepare bacterial lysates, a suspension ($A_{600}$=0.6) of *H. pylori* cells was prepared in 200 µl of sterile distilled water. Samples were boiled in a water bath for 5 min, cooled on ice, and centrifuged at 15,000 rpm for 5 min. Suspensions containing liberated DNA were stored at −20° C. and 10 µl were used per PCR reaction.

PCR reactions were carried out in 50 μg of an amplification reaction mixture containing 350 pmol of each primer (degenerated oligonucleotides), 10 mM Tris-HCl pH 8.3, 50 mM KCl, 1.5 mM $MgCl_2$, 0.2 mM of each deoxynucleotide, 10 μl of a DNA preparation and 2.5 Units of Taq DNA polymerase. PCR consisted of 25 cycles of the following program: 94° C. for 2 min, 50° C. for 2 min, and 72° C. for 2 min.

Direct sequencing of the PCR products was achieved following treatment of the PCR products (7 μl) with 10 units of Exonuclease I and 1 unit of Shrimp Alkaline Phosphatase according to the manufacturer's instructions (Sequenase PCR Product Sequencing kit, Amersham). 100 pmoles of each oligonucleotide H36 and H37 were used for sequencing.

Samples were loaded on a 6% acrylamide gel and run in Taurine Buffer (0.1 M Tris-base, 0.03 M Taurine, 0.5 mM EDTA).

1.5 Hybridization

Colony blots for screening of the H pylori cosmid bank were prepared on nitrocellulose membranes according to the procedure of Sambrook et al. (1989) as were the Southern blots. Radioactive labeling of PCR products was performed by random priming with $\alpha^{32}P(dCTP)$ using the Megaprime DNA system (Amersham). Colony hybridizations were performed under high stringency conditions (5×SSC, 0.1% SDS, 50% formamide, 42° C.). Southern hybridizations were performed under high stringency conditions (5×SSC, 2×Denhardt's Solution, 0.02% ATP, 0.1%SDS) at 65° C. After hybridization, filters were washed 2 times for 5 minutes at room temperature with a solution of 1×SSC, 0.1% SDS (w/v), and 2 times at 65° C. with a solution of 0.1×SSC, 0.1% SDS.

1.6 Measurement of the Amidase Activity

An amidase activity assay was adapted from the urease assay described by Cussac et al. (1992), which made use of the Berthelot Reaction. A very similar enzymatic assay has previously been described for amidase activity determination (Silman et al., 1989). Amidase activity was measured as the release of ammonia after cleavage from its amide substrate.

Bacteria were harvested in 2 ml of PEB (100 mM phosphate buffer pH 7.4, 10 mM EDTA) and washed 2 times in the same buffer. To prepare sonicated extracts, cells were disrupted by four 30 sec bursts with a Branson Sonifier at 30 W at a 50% cycle. Cell debris was removed by centrifugation prior to the amidase assay. Protein concentration of the sonicated extracts was determined with a commercial version of the Bradford Assay (Sigma Chemicals).

Samples (5 to 50 μl) were added to 200 μl of an amide substrate solution. Acrylamide, acetamide, propionamide, formamide, isobutyramide, and nicotinamide were used as substrate at 100 mM in PEB. The reaction was carried out at room temperature for up to 30 min. The reaction mixture was then treated by addition of 400 μl of phenol-nitroprusside reagent and the color was developed by the addition of 400 μl of alkaline hypochlorite reagent after 6 min incubation at 50° C. Reaction mixture blanks, in which the amidase activity was inactivated by boiling 5 min prior to addition of substrate, were treated in the same way. The absorbance was read 625 nm. The amount of ammonia released was determined from a standard curve. One unit of the amidase activity was defined as the amount of enzyme required for the formation of one μmol of ammonia from the substrate per min per mg of total proteins.

1.7 Computer Work

DNA and protein sequences were treated with the DNA Strider (1.2) program. Searches in the data banks and sequence alignments were performed with the Genetics Computer Group Sequence Analysis Software Package, version 7-UNIX.

2.1 Microsequencing of the N-terminus of Two Internal Peptides of a H. pylori Protein A systematic analysis of the amino acid sequence of H. pylori proteins was performed after separation of whole H. pylori 85P proteins by two-dimensional denaturing gel electrophoresis. One spot corresponding to a protein with an apparent molecular mass of 49 kDa was detected, purified, and endoproteolysed. The N-terminus of two major products were microsequenced and the corresponding peptidic sequences were analyzed. The two amino acid sequences (FIG. 1) show strong similarity with the P. aeruginosa and Rhodococcus sp. R312 aliphatic amidases. This suggested the existence of an aliphatic amidase in H. pylori. A pair of degenerate oligonucleotides, H36 and H37 (FIG. 1), were deduced from this sequence based on the H. pylori codon usage.

2.2 PCR-Amplification of an Internal Amidase Sequence with H36 and H37 Degenerated Oligonucleotides PCR-amplification was performed with oligonucleotides H36 and H37 on chromosomic DNA of two different H pylori strains, N6 and 85P. A single 240 bp-PCR-product was visualized on agarose gel with both strains and the nucleotide sequence of the PCR-fragment generated from strain 85P was determined (FIG. 2). The deduced amino acid sequence encoded by this PCR fragment (FIG. 2) was very similar to an internal sequence of the P. aeruginosa and Rhodococcus sp. R312 amidases. Boiled bacterial lysates of 45 clinical isolates of H. pylori were used for PCR-amplification with oligonucleotides H36 and H37. A single 240 bp-product was generated by gene amplification in all the lysates tested suggesting that amidase is a common trait to all H. pylori isolates.

2.3 Screening of a H. pyloric Genomic Library and Identification of a Cosmid (IIIG5) carrying the Complete Amidase Gene of H. pylori A cosmid library of H. pylori strain 85P was previously constructed in our laboratory (Labigne et al., 1991). The 240 bp-DNA fragment generated by PCR using H36 and H37 was randomly labeled with $\alpha^{32}P(dCTP)$ and used as a probe to screen the 480 clones of the H. pylori genomic library for colony hybridization. Only the colony harboring cosmid IIIG5 (Labigne et al., 1991) showed clear hybridization. The purified IIIG5 cosmid used as a template in PCR-amplification using the H36 and H37 oligonucleotides generated a single 240 bp-fragment.

2.4 Southern Blot Analysis of the Amidase Gene on the H. pylori N6 and 85P Genomic DNA and on Cosmid IIIG5

The same probe corresponding to an internal segment of the amidase encoding gene was Southern hybridized on HindIII-restricted DNA from the H. pylori strains N6 and 85P, and from cosmid IIIG5. Hybridization with a single and identical 2.6 kb HindIII restriction fragment was obtained with cosmid IIIG5 and with 85P genomic DNA. This suggested the existence of a single gene coding for an aliphatic amidase in H pylori and confirmed that the PCR-amplified DNA fragment was indeed amplified from *H. pylori*. The same probe hybridized to two HindIII restriction fragments of the N6 genomic DNA; this indicates that in N6, the amidase gene sequence is slightly different and that this difference is associated with the presence of an HindIII restriction site.

2.5 Subcloning of a DNA Fragment Carrying the Entire Amidase Gene

Figure 3B:
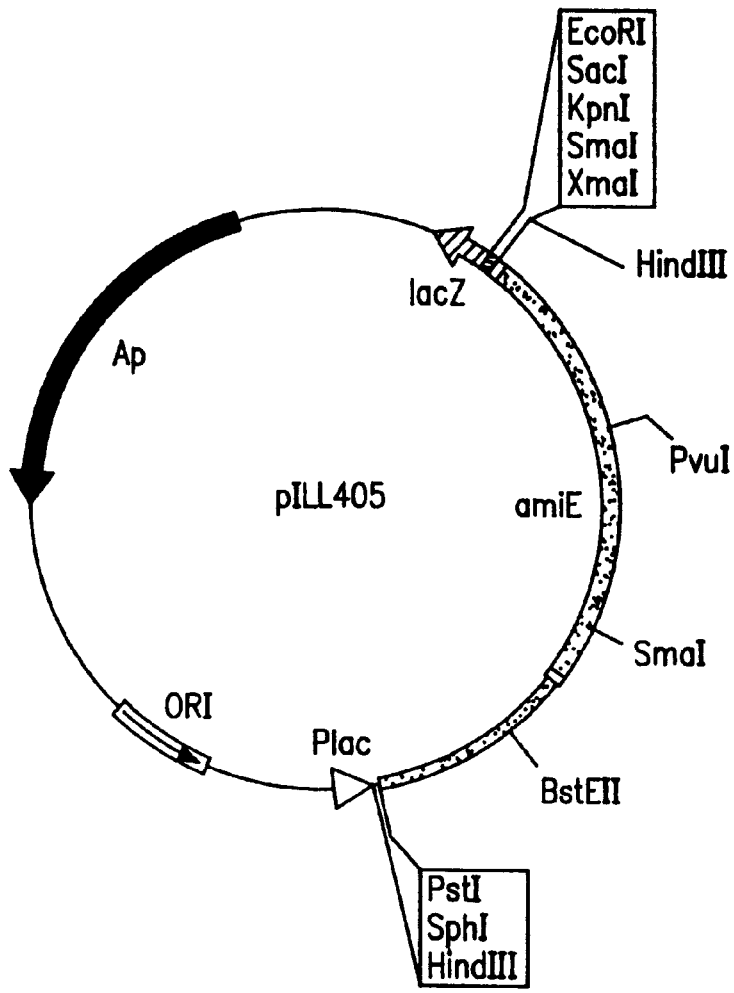

The 2.6 kb-HindIII fragment hybridizing with the PCR-generated probe was subcloned into the HindIII site of vector pILL570 (Labigne et al., 1991). The resulting plasmid was designated pILL400 (FIG. 3a). Several subclones generated from pILL400 were constructed using vector pUC19 (Yanisch-Perron et al., 1985). The smallest plasmid still able to produce the 240 bp-PCR-fragment with H36-H37, and that was likely to contain the entire amidase gene, was selected and designated pILL405. This plasmid carries a 1.5 kb Xhol-Bg/II fragment of *H. pylori* DNA and its restriction map is shown in FIG. 3b.

Plasmid pILL405 was deposited with the Collection Nationale de Cultures de Microorganismes (CNCM) under number I-1863 on Mar. 18, 1997.

Figures 3, 4B:
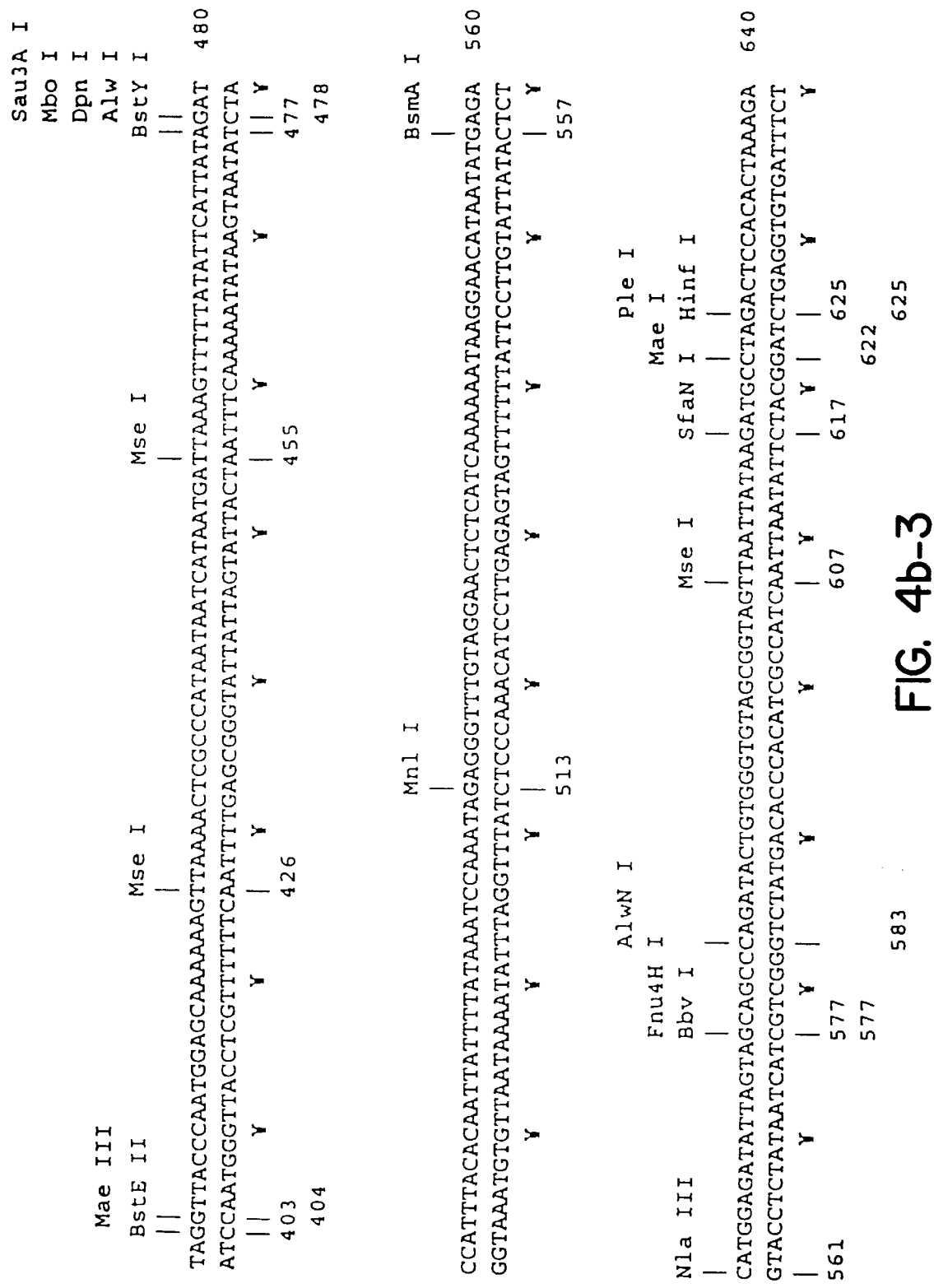
Figures 4, 4B, 5:
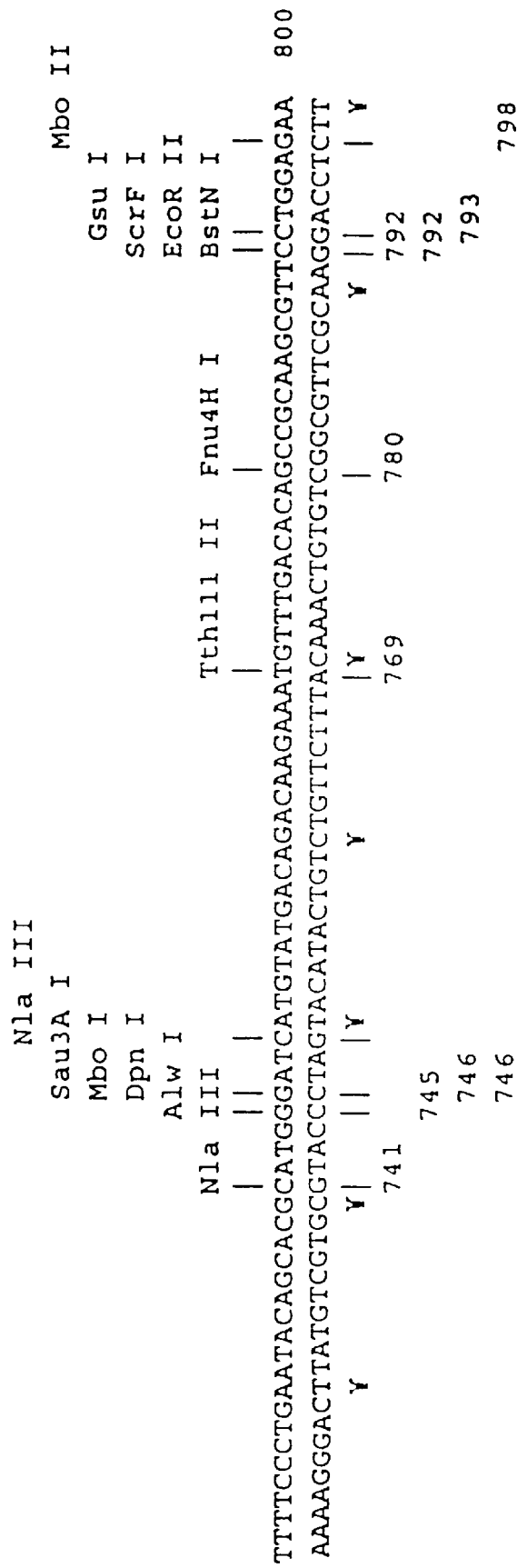
Figures 4, 4B, 5, 6:
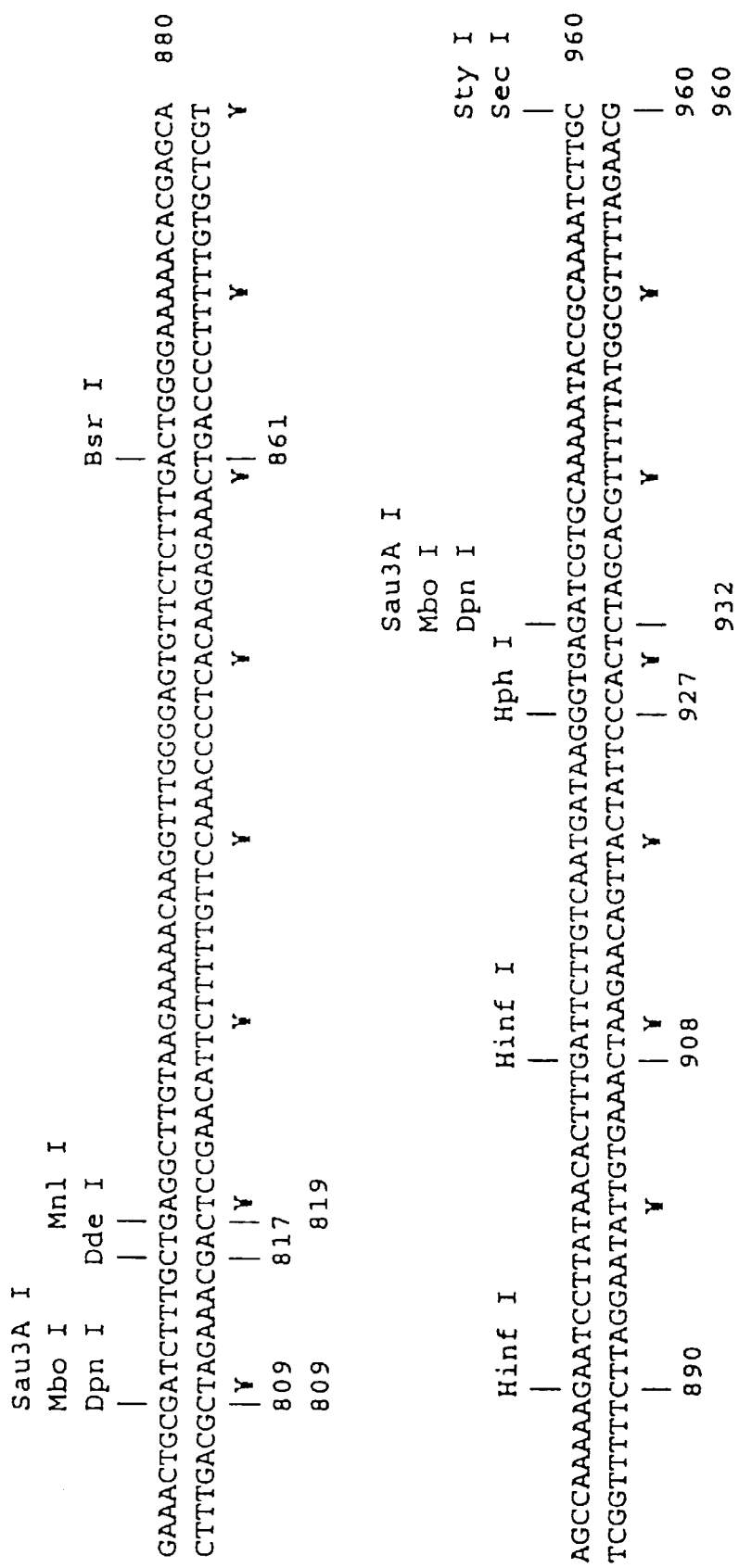

2.6 Determination of the Nucleotide Sequence of the *H. pylori* Amidase Gene amiE and Comparison of AmiE with its Homologs A DNA preparation of plasmid pILL405 was sent to the "Institut d'Analyses Génétiques, Genome express SA" for nucleotide sequence determination of the 1520 bp *H. pylori* DNA insert (automatic sequencer, Applied Biosystems) (FIG. 4a). The 1520 bp-insert included a 1017 bp-long open reading frame (ORF) coding for a protein of 339 amino acids with a calculated molecular mass of 37,746 da (FIG. 5). The amino acid sequence deduced from this ORF was very similar to the *P. aeruginosa* and Rhodococcus sp. R312 amidases, with as much as 75% of identity with each of them (FIG. 6). The DNA sequence of the *H. pylori* amiE gene has 65% homology with the amidase genes of *P. aeruginosa* and Rhodococcus sp. R3 12. This confirmed that the encoded protein is indeed an aliphatic amidase. The 1017 bp-ORF was designated amiE and the corresponding protein AmiE.

Figures 4, 4B, 5, 6, 7, 8, 9:
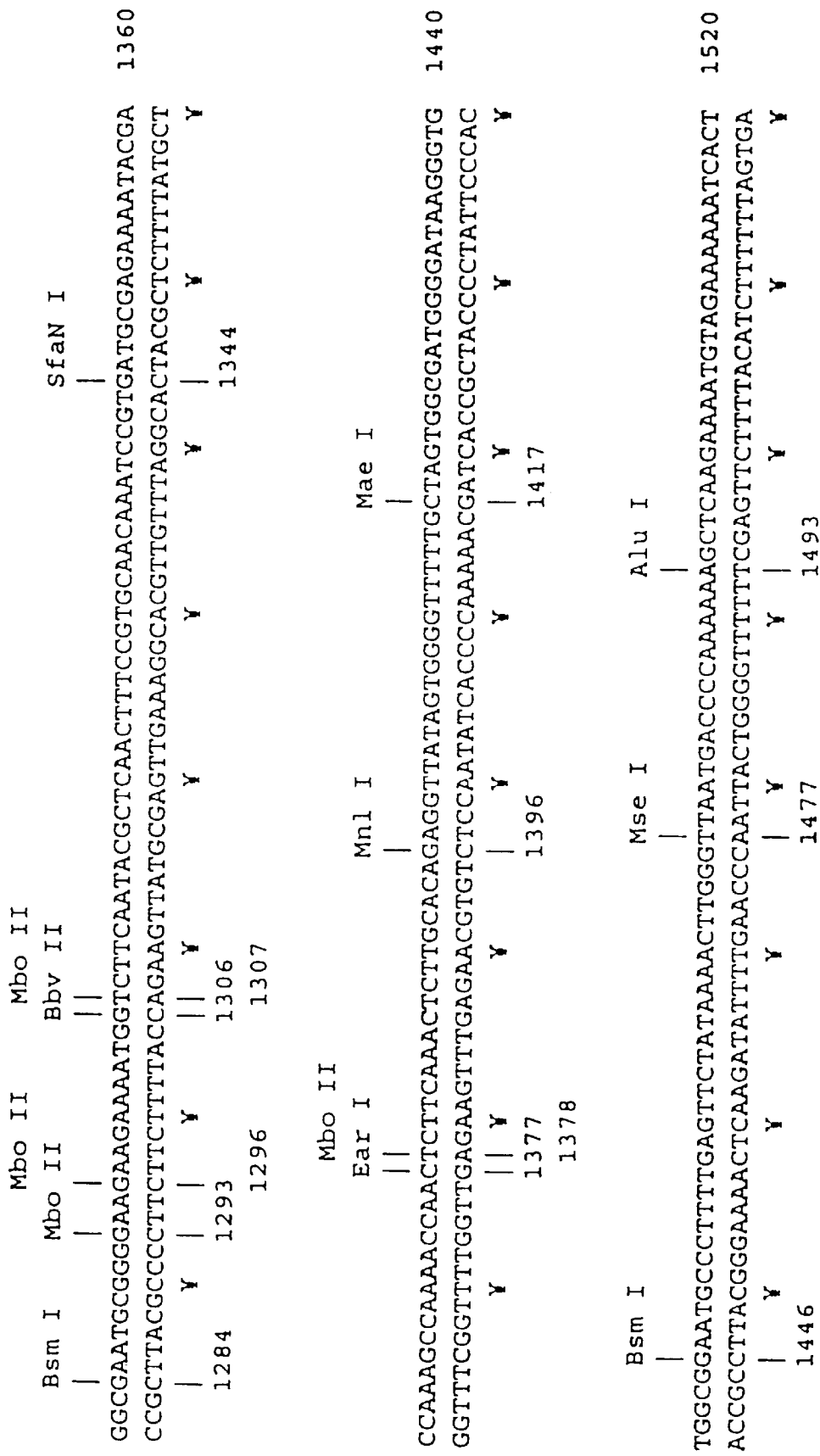
Figures 4, 4B, 5, 6, 7, 8, 9, 10:
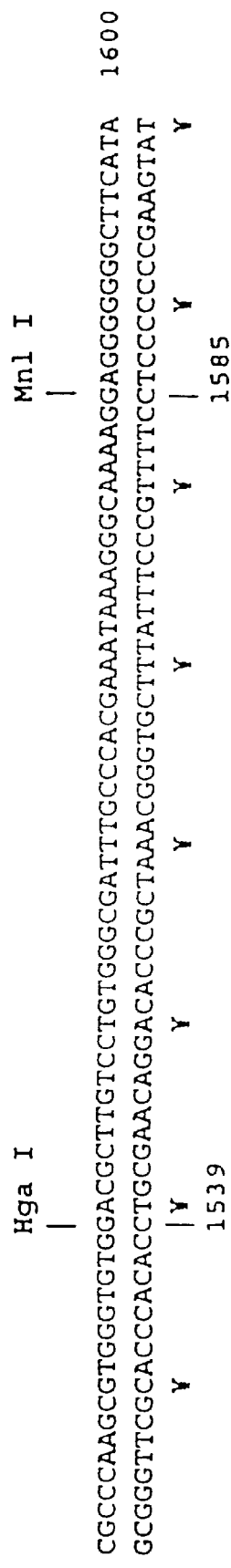

A truncated ORF situated upstream from the amiE gene, corresponding to the 3'- extremity of another Helicobacter gene, has also been detected (FIG. 7). No homologs of the deduced protein could be found in the data banks.

2.7 Overproduction of the *H. pylori* Amidase

Figure 3C:
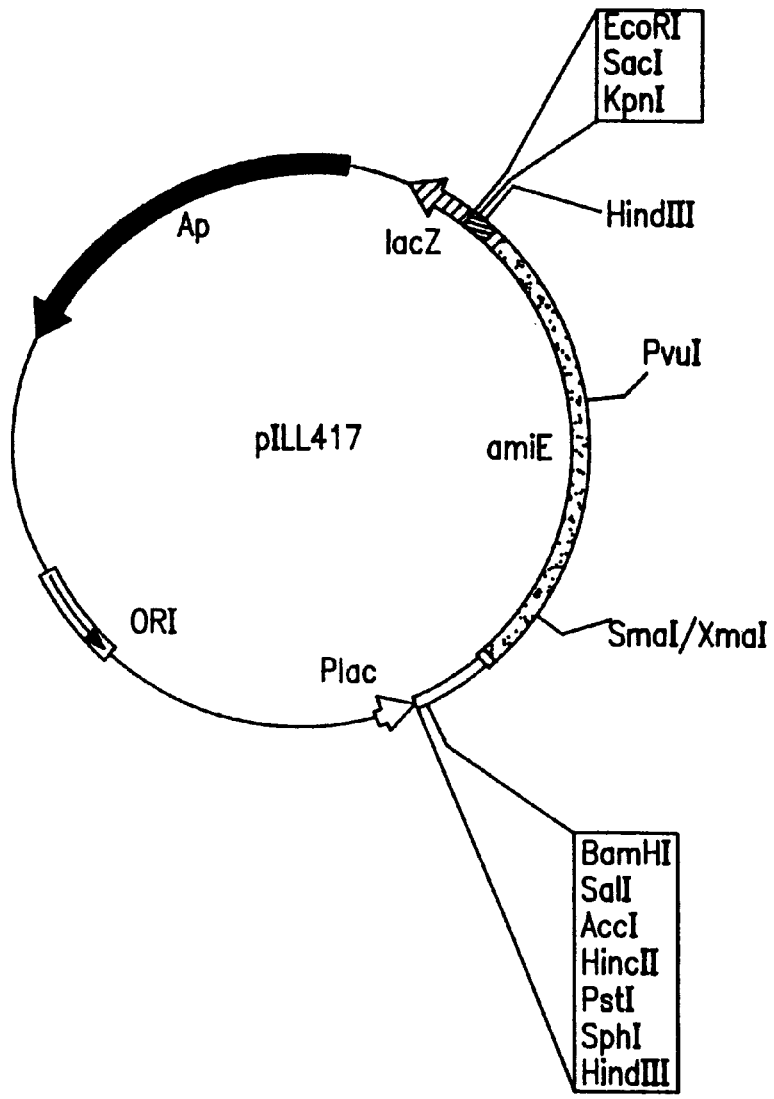

In order to overexpress the *H. pylori* amidase, the amiE gene was put under control of the Plac promoter of the high copy number vector pUC19 by cloning the EcoRI-BstEII fragment from pILL405 into the EcoRI-Smal sites of pUC19. The resulting plasmid was designated pILL417 (FIG. 3c). The proteins expressed by the *E. coli* strain MC1061 harboring either pILL417 or pUC19 grown overnight in liquid Luria medium, were examined and compared by SDS-PAGE. The amiE gene product was visualized as a large band corresponding to a protein with an apparent molecular mass of 40 kDa. The H pylon amidase can thus be stably overproduced in *E. coli* without affecting cell viability.

Plasmid pILL417 was deposited with the Collection Nationale de Cultures de Microorganismes (CNCM) under number 1-1864 on Mar. 27, 1997.

2.8 Amidase Activity and Substrate Specificity in *H. pylori* and in Recombinant *E. coli* strains Amidase activity was measured as the release of ammonia after cleavage from its amide substrate. Substrate specificity of *H. pylori* amidase was tested with crude extracts of *H. pylori* strain N6. Amidase activity was approximately 6 units (U) for acrylamide, 5 U for propionamide, 3 U for acetamide, and was very low for formamide (0.1U) and isobutyramide (0.02U). No activity was detected on nicotinamide. Amidase activity was also measured on crude extracts of *E. coli* recombinant strains. Strain MC 1061 carrying plasmid pILL405 has an amidase activity on acrylamide of 100 U; the *H. pylori* amidase is thus fully active in *E. coli*. The high activity level of MC1060(pILL405) compared to that of *H. pylori* resulted from the expression of amiE under the control of the Plac promoter and probably also from the high copy number of this plasmid. Urea, although structurally related to amides, is not hydrolyzed by the *H. pylori* amidase expressed in strain MC1061 (pILL405). In addition, a *H. pylori* urease negative mutant (N6-ureB) is not affected in its amidase activity. These results suggest that there is no obvious interference in ammonia release due to the activity of the two enzymes (amidase and urease).

Figure 3D:
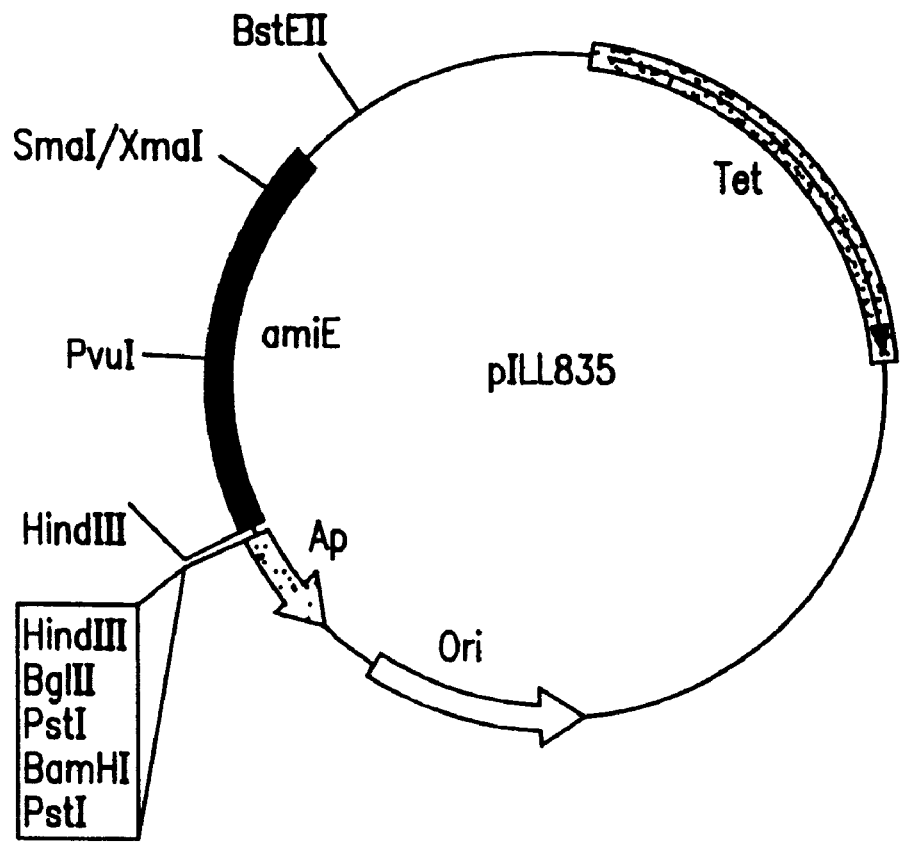
Figure 3E:
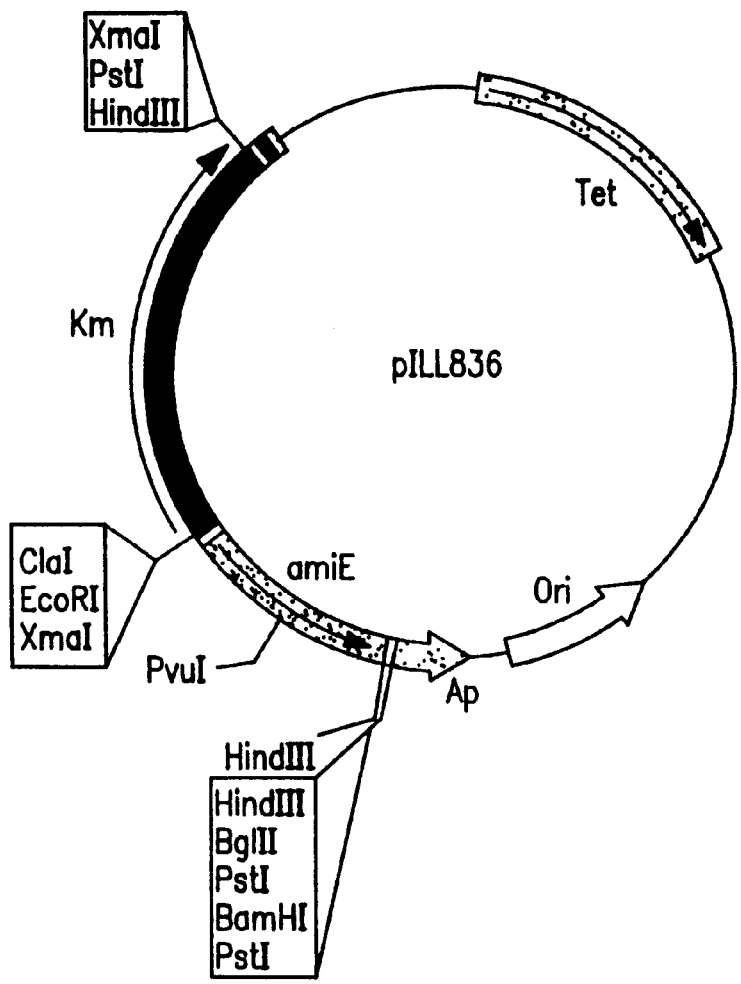

2.9 Construction of a N6-836 *H. pylori* Mutant Carrying a Disrupted amiE Gene A *H. pylori* mutant carrying a disrupted amiE gene was constructed by allelic exchange. In order to obtain a plasmid with a unique Xmal restriction site situated within the amiE open reading frame (at 147 bp from its initiation codon), we constructed plasmid pILL835 (FIG. 3d). This plasmid carries the Pstl-Ahol restriction fragment of plasmid pILL405 (containing the 1.5 kb *H. pylori* DNA insert) cloned into the Pstl-Sspl restriction sites of pBR322. Plasmid pILL836 (FIG. 3e) resulted from the introduction of a 1.5 kb-fragment carrying a kanamycin resistance [aph(3')-III] gene under control of its own promoter (Trieu-Cuot et al., 1985), into the Xmal site of plasmid pILL835. A concentrated DNA preparation of pILL836 was used to transform *H. pylori* strain N6 by electroporation. *H. pylori* transformants resistant to 20 µg/ml of kanamycin were selected on plates. All of the eight transformants examined carried an amiE gene disrupted by the kanamycin gene attesting to allelic exchange between the mutated amiE allele of pILL836 and the chromosomic amiE copy. The correct insertion of the cassette in the amiE gene on the chromosome was controlled by PCR with primers corresponding to sequences flanking the Xmal restriction site within the amiE gene and divergent primers corresponding to sequences within the kanamycin resistance gene. One of these strains was further studied and designated N6-836. No amidase activity on acrylamide was detected in the amidase negative mutant N6-836.

The growth rate of this amidase negative mutant N6-836 on blood agar medium (a rich medium) was not significantly affected when compared to that of the parental strain N6. The amidase function is thus not essential for *H. pylori* growth in vitro.

To determine whether the amiE gene is essential for *H. pylori* survival and colonization in its natural environment, the gastric mucosa, the same mutation is introduced into the amiE gene of the *H. pylori* SS1 strain (Sydney Strain; Buck et al., 1996) used in a *H. pylori*/mouse model. Colonization and local inflammation are compared after infection of mice with the *H. pylori* parental strain and its amidase mutant.

REFERENCES

1. Asano, Y., Tachibana, M., Tani, Y. & Yamada, H. (1982), Purification and characterization of amidase which participates in nitrile degradation. *Agric. Biol. Chem.*, 46, 1175–1181.

2. Brammar, W. J., Charles, I. G., Matfield, M., Cheng-Pin, L., Drew, R. E. & Clarke, P. H. (1987), The nucleotide sequence of the amiE gene of *Pseudomonas aeruginosa*. *FEBS Letters;* 215, 291–294.
3. Brown, P. R. & Tata, R. (1987), Isolation of amidase-negative mutants of *Pseudomonas aeruginosa* using glycollamide as a selective agent. *J. Gen. Microbio.,* 133, 1527–1533.
4. Buck, F. J., Radcliff, F. J., O'Rourke, J., Lee, A. & Doidge, C. (1996), The "Sydney Strain" of *H. pylori*. A new standard for vaccine studies in mice? *Gut,* 39, Abstract 1B:03.
5. Casadaban, M. & Cohen, S. N. (1980), Analysis of gene control signals by DNA fusions and cloning in *E. coli. J. Mol. Biol.,* 138, 179–207.
6. Clarke, P. H. (1984) Amidases of *Pseudomonas aeruginosa*. In: Mortlock, R. P. (Ed.), Microorganisms as Model System for Studying Evolution. Plenum Press, New York, pp. 187–231.
7. Cussac, V., Ferrero, R. L. & Labigne, A. (1992) Expression of *Helicobacter pylori* urease genes in *Escherichia coli* grown under nitrogen-limiting conditions. *J. Bacteriol.,* 174, 2466–2473.
8. Ferrero, R. L, Cussac, V., Courcoux, P. & Labigne, A. (1992), Construction of isogenic urease-negative mutants of *Helicobacter pylori* by allelic exchange. *J. Bacteriol.,* 174, 4212–4217.
9. Ferrero, R. L., Thiberge, J.-M., Kansau, I., Wuscher, N., Huerre, M. & Labigne, A. (1995), The GroES homolog of *Helicobacter pylori* confers protective immunity against mucosal infection in mice *Proc. Natl. Acad. Sci. U.S.A.,* 92, 6499–6503.
10. Friedrich, C. G. & Mitrenga, G. (1981), Utilization of aliphatic amides and formation of two different amidases by *Alcaligenes eutrophus. J. Gen. Microbiol.,* 125, 367–374.
11. Labigne, A., Cussac, V. & Courcoux, P. (1991), Shuttle cloning and nucleotide sequence of *Helicobacter pylori* genes responsible for urease activity. *J. Bacteriol.,* 173, 1920–1931.
12. Miller, J. H. (1992), *A short course in Bacterial Genetics: A laboratory manual and handbook for Escherichia coli and related bacteria*. Cold Spring Harbor, N.Y.: Cold Spring Harbor Laboratory.
13. Nagasawa, T. and Yamada, H. (1989) "Microbial Transformation of Nitriles," *Trends in Biotechnology,* 7, 153–158.
14. Nawaz, M. S., Khan, A. A., Seng, J. E., Leakey, J. E., Siitonen, P. H. & Cerniglia, C. E. (1994), Purification and characterization of an amidase from an acrylamide-degradating, Rhodooccus sp. *Appl. Environ. Microbiol.,* 60, 3343–3348.
15. Nawaz, M. S., Khan, A. A., Bhattacharayya, D., Siitonen, P. H. & Cerniglia, C. E. (1996), Physical, biochemical, and immunological characterization of a thermostable amidase from *Klebsiella pneumoniae* NCTR 1. *Journal of Bacteriology,* 178, 2397–2401.
16. Novo, C., Tata, R., Clemente, A. & Brown, P. R. (1995), *Pseudomonas aeruginosa* aliphatic amidase is related to the nitrilase/cyanide hydratase enzyme family and $Cys^{166}$ is predicted to be the active site nucleophile of the catalytic mechanism. *FEBS Lett.,* 367, 275–279.
17. Roberts, T. R. (1984), Non extractable pesticide residues in soils and plants. *Pure Appl. Chem.,* 56, 945–956.
18. Sambrook, J., Fritsch, E. F. & Maniatis, T. (1989) *Molecular cloning: a Laboratory Manual,* 2nd ed. Cold Spring Harbor, N.Y.: Cold Spring Harbor Laboratory.
19. Silman, N., Carver, M. A. & Jones, C. W. (1991), Directed evolution of amidase in *Methylophilus methylotrophus;* purification and properties of amidases from wild-type and mutant strains. *J. Gen. Microbiol.,* 137, 169–178.
20. Silman, N. J., Carver, M. A. & Jones, C. W. (1989), Physiology of amidase production by *Methylophilus methylotrophus:* isolation of hyperactive strains using continuous culture. *J. Gen. Microbiol.,* 135, 3153–3164.
21. Soubrier, F., Levy-Schil, S., Mayaux, J.-F., Petre, D., Amaud, A. & Crouzet, J. (1992), Cloning and primary structure of the wide-spectrum amidase from Brevibacterium sp. R312: high homology to the amiE product from *Pseudomonas aeruginosa. Gene,* 116, 99–104.
22. Southern, E. M. (1975), Detection of specific sequences among DNA fragments separated by gel electrophoresis, *J. Mol. Biol.* 98, 503–517.
23. Trieu-Cuot, P., Gerbaud, G., Lambert, T. & Courvalin, P. (1985) In vivo transfer of genetic information between Gram-positive and Gram-negative bacteria. *EMBO J.,* 4, 3583–3587.
24. Yanisch-Perron, C., Vieira, J. & Messing, J. (1985), Improved M13 phage cloning vectors and host strains: nucleotide sequence of M13mp18 and pUC19 vectors. *Gene,* 33, 103–119.

```
SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:1:
```

Val Trp Gly Val Phe Ser Leu Thr Gly Glu Lys
1               5                   10

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate primer"

(ix) FEATURE:
        (A) NAME/KEY: modified_base
        (B) LOCATION: one-of(3, 9, 12, 18, 21, 24)
        (D) OTHER INFORMATION: /mod_base= i (xi) SEQUENCE DESCRIPTION: SEQ ID NO:2:

GTNTGGGGNG TNTTYWSNYT NACNGG                                         26

(2) INFORMATION FOR SEQ ID NO:3:

(i) SEQUENCE CHARACTERISTICS:
        (A) LENGTH: 15 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Val Ser Leu Ile Ile Cys Asp Asp Gly Asn Tyr Pro Glu Ile Trp
1               5                   10                  15

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate primer"

(ix) FEATURE:
        (A) NAME/KEY: modified_base
        (B) LOCATION: one-of(4, 10, 19)
        (D) OTHER INFORMATION: /mod_base= i (xi) SEQUENCE DESCRIPTION: SEQ ID NO:4:

CCANATYTCN GGRTARATNC CRTCRTCRC                                      29

(2) INFORMATION FOR SEQ ID NO:5:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..147

(xi) SEQUENCE DESCRIPTION: SEQ ID NO:5:

```
AAT CCT TAT AAC ACT TTG ATT CTT GTC AAT GAT AAG GGT GAG ATC GTG      48
Asn Pro Tyr Asn Thr Leu Ile Leu Val Asn Asp Lys Gly Glu Ile Val
 1               5                  10                  15

CAA AAA TAC CGC AAA ATC TTG CCT TGG TGC CCT ATT GAA TGT TGG TAT      96
Gln Lys Tyr Arg Lys Ile Leu Pro Trp Cys Pro Ile Glu Cys Trp Tyr
            20                  25                  30

CCT GGG GAT AAA ACT TAT GTG GTT GAT GGG CCT AAG GGC TTG AAA GTT     144
Pro Gly Asp Lys Thr Tyr Val Val Asp Gly Pro Lys Gly Leu Lys Val
        35                  40                  45

TCT                                                                 147
Ser
```

(2) INFORMATION FOR SEQ ID NO:6:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:6:

```
Asn Pro Tyr Asn Thr Leu Ile Leu Val Asn Asp Lys Gly Glu Ile Val
 1               5                  10                  15

Gln Lys Tyr Arg Lys Ile Leu Pro Trp Cys Pro Ile Glu Cys Trp Tyr
            20                  25                  30

Pro Gly Asp Lys Thr Tyr Val Val Asp Gly Pro Lys Gly Leu Lys Val
        35                  40                  45

Ser
```

(2) INFORMATION FOR SEQ ID NO:7:

(i) SEQUENCE CHARACTERISTICS:
        (A) LENGTH: 1675 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TTGTGTGGAA TTGTGAGCGG ATAACAATTT CACACAGGAA ACAGCTATGA CCATGATTAC      60

GCCAAGCTTG CATGCCTGCA GGTCGAGCGC TCATTAAAAA AGGCGTTGTT TTTGATGAAA     120

TCTTTTATAA CCAGGATTTG GAACTCACTG AGGGCGCTAG GAGCAATCTT GTTTTAGAAA     180

TCCATAACAG GCTTTTAACC CCTTATTTTA GCGCGGGCGC GTTAAACGGG ACGGGTGTTG     240

TGGGGTTGTT AAAAAAGGGT CTTGTTGGGC ATGCCCCTTT GAAATTGCAA GACTTGCAAA     300

GAGCGGCTAA AATCTATTGC ATTAACGCGC TATATGGCTT AGTGGAAGTG AAAATCAAAT     360

AACCATAAAA ATAGAGCAAC TAAAACCTCA TTTTTAGAAA TAGGTTACCC AATGGAGCAA     420

AAAAGTTAAA ACTCGCCCAT AATAATCATA ATGATTAAAG TTTTTATATT CATTATAGAT     480

CCATTTACAC AATTATTTTA TAAATCCAAA TAGAGGGTTT GTAGGAACTC TCATCAAAAA     540

ATAAGGAACA TAATATGAGA CATGGAGATA TTAGTAGCAG CCCAGATACT GTGGGTGTAG     600

CGGTAGTTAA TTATAAGATG CCTAGACTCC ACACTAAAGA ACAAGTGTTG GAAAATTGTC     660

GCAATATCGC TAAGGTGATT GGTGGGGTCA ACAGGGTTT GCCCGGGTTG GATCTGATTA     720

TTTTCCCTGA ATACAGCACG CATGGGATCA TGTATGACAG ACAAGAAATG TTTGACACAG     780

CCGCAAGCGT TCCTGGAGAA GAAACTGCGA TCTTTGCTGA GGCTTGTAAG AAAAACAAGG     840
```

-continued

```
TTTGGGGAGT GTTCTCTTTG ACTGGGAAA AACACGAGCA AGCCAAAAAG AATCCTTATA      900

ACACTTTGAT TCTTGTCAAT GATAAGGGTG AGATCGTGCA AAAATACCGC AAAATCTTGC     960

CTTGGTGCCC TATTGAATGT TGGTATCCTG GGGATAAAAC TTATGTGGTT GATGGGCCTA    1020

AGGGCTTGAA AGTTTCTTTG ATCATTTGCG ATGATGGGAA CTACCCTGAA ATTTGGCGCG    1080

ATTGCGCGAT GCGTGGGGCA GAACTCATTG TGCGCTGTCA AGGTTACATG TATCCGGCTA    1140

AGGAGCAACA AATTGCGATC GTGAAAGCTA TGGCGTGGGC CAATCAATGT TATGTAGCGG    1200

TAGCGAATGC GACCGGTTTT GATGGGGTGT ATTCCTATTT TGGGCATTCT AGCATTATTG    1260

GTTTTGATGG GCATACTTTG GGCGAATGCG GGGAAGAAGA AAATGGTCTT CAATACGCTC    1320

AACTTTCCGT GCAACAAATC CGTGATGCGA GAAAATACGA CCAAAGCCAA AACCAACTCT    1380

TCAAACTCTT GCACAGAGGT TATAGTGGGG TTTTTGCTAG TGGCGATGGG GATAAGGGTG    1440

TGGCGGAATG CCCTTTTGAG TTCTATAAAA CTTGGGTTAA TGACCCCAAA AAAGCTCAAG    1500

AAAATGTAGA AAAAATCACT CGCCCAAGCG TGGGTGTGGA CGCTTGTCCT GTGGGCGATT    1560

TGCCCACGAA ATAAAGGGCA AAAGGAGGGG GGGCTTCATA GAAGCTTCTA GAGATCCCCG    1620

GGTACCGAGC TCGAATTCAC TGGCCGTCGT TTTACAACGT CGTGACTGGG AAAAC         1675
```

(2) INFORMATION FOR SEQ ID NO:8:

(i) SEQUENCE CHARACTERISTICS:
        (A) LENGTH: 1520 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

```
GGTCGAGCGC TCATTAAAAA AGGCGTTGTT TTTGATGAAA TCTTTTATAA CCAGGATTTG      60

GAACTCACTG AGGGCGCTAG GAGCAATCTT GTTTTAGAAA TCCATAACAG GCTTTTAACC     120

CCTTATTTTA GCGCGGGCGC GTTAAACGGG ACGGGTGTTG TGGGGTTGTT AAAAAAGGGT     180

CTTGTTGGGC ATGCCCCTTT GAAATTGCAA GACTTGCAAA GAGCGGCTAA AATCTATTGC     240

ATTAACGCGC TATATGGCTT AGTGGAAGTG AAAATCAAAT AACCATAAAA ATAGAGCAAC     300

TAAAACCTCA TTTTTAGAAA TAGGTTACCC AATGGAGCAA AAAGTTAAA ACTCGCCCAT      360

AATAATCATA ATGATTAAAG TTTTTATATT CATTATAGAT CCATTTACAC AATTATTTTA     420

TAAATCCAAA TAGAGGGTTT GTAGGAACTC TCATCAAAAA ATAAGGAACA TAATATGAGA     480

CATGGAGATA TTAGTAGCAG CCCAGATACT GTGGGTGTAG CGGTAGTTAA TTATAAGATG     540

CCTAGACTCC ACACTAAAGA ACAAGTGTTG GAAAATTGTC GCAATATCGC TAAGGTGATT     600

GGTGGGGTCA AACAGGGTTT GCCCGGGTTG GATCTGATTA TTTTCCCTGA ATACAGCACG     660

CATGGGATCA TGTATGACAG ACAAGAAATG TTTGACACAG CCGCAAGCGT TCCTGGAGAA     720

GAAACTGCGA TCTTTGCTGA GGCTTGTAAG AAAAACAAGG TTTGGGGAGT GTTCTCTTTG     780

ACTGGGAAA AACACGAGCA AGCCAAAAAG AATCCTTATA ACACTTTGAT TCTTGTCAAT     840

GATAAGGGTG AGATCGTGCA AAAATACCGC AAAATCTTGC CTTGGTGCCC TATTGAATGT     900

TGGTATCCTG GGGATAAAAC TTATGTGGTT GATGGGCCTA AGGGCTTGAA AGTTTCTTTG     960

ATCATTTGCG ATGATGGGAA CTACCCTGAA ATTTGGCGCG ATTGCGCGAT GCGTGGGGCA    1020

GAACTCATTG TGCGCTGTCA AGGTTACATG TATCCGGCTA AGGAGCAACA AATTGCGATC    1080

GTGAAAGCTA TGGCGTGGGC CAATCAATGT TATGTAGCGG TAGCGAATGC GACCGGTTTT    1140
```

-continued

```
GATGGGGTGT ATTCCTATTT TGGGCATTCT AGCATTATTG GTTTTGATGG GCATACTTTG      1200

GGCGAATGCG GGGAAGAAGA AAATGGTCTT CAATACGCTC AACTTTCCGT GCAACAAATC      1260

CGTGATGCGA GAAATACGA CCAAAGCCAA ACCAACTCT TCAAACTCTT GCACAGAGGT        1320

TATAGTGGGG TTTTTGCTAG TGGCGATGGG GATAAGGGTG TGGCGGAATG CCCTTTTGAG      1380

TTCTATAAAA CTTGGGTTAA TGACCCCAAA AAAGCTCAAG AAAATGTAGA AAAAATCACT      1440

CGCCCAAGCG TGGGTGTGGA CGCTTGTCCT GTGGGCGATT TGCCCACGAA ATAAAGGGCA     1500

AAAGGAGGGG GGGCTTCATA                                                  1520
```

(2) INFORMATION FOR SEQ ID NO:9:

(i) SEQUENCE CHARACTERISTICS:
        (A) LENGTH: 1020 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1017

(xi) SEQUENCE DESCRIPTION: SEQ ID NO:9:

```
ATG AGA CAT GGA GAT ATT AGT AGC AGC CCA GAT ACT GTG GGT GTA GCG       48
Met Arg His Gly Asp Ile Ser Ser Ser Pro Asp Thr Val Gly Val Ala
 1               5                  10                  15

GTA GTT AAT TAT AAG ATG CCT AGA CTC CAC ACT AAA GAA CAA GTG TTG       96
Val Val Asn Tyr Lys Met Pro Arg Leu His Thr Lys Glu Gln Val Leu
                20                  25                  30

GAA AAT TGT CGC AAT ATC GCT AAG GTG ATT GGT GGG GTC AAA CAG GGT      144
Glu Asn Cys Arg Asn Ile Ala Lys Val Ile Gly Gly Val Lys Gln Gly
             35                  40                  45

TTG CCC GGG TTG GAT CTG ATT ATT TTC CCT GAA TAC AGC ACG CAT GGG      192
Leu Pro Gly Leu Asp Leu Ile Ile Phe Pro Glu Tyr Ser Thr His Gly
         50                  55                  60

ATC ATG TAT GAC AGA CAA GAA ATG TTT GAC ACA GCC GCA AGC GTT CCT      240
Ile Met Tyr Asp Arg Gln Glu Met Phe Asp Thr Ala Ala Ser Val Pro
 65                  70                  75                  80

GGA GAA GAA ACT GCG ATC TTT GCT GAG GCT TGT AAG AAA AAC AAG GTT      288
Gly Glu Glu Thr Ala Ile Phe Ala Glu Ala Cys Lys Lys Asn Lys Val
                 85                  90                  95

TGG GGA GTG TTC TCT TTG ACT GGG GAA AAA CAC GAG CAA GCC AAA AAG      336
Trp Gly Val Phe Ser Leu Thr Gly Glu Lys His Glu Gln Ala Lys Lys
                100                 105                 110

AAT CCT TAT AAC ACT TTG ATT CTT GTC AAT GAT AAG GGT GAG ATC GTG      384
Asn Pro Tyr Asn Thr Leu Ile Leu Val Asn Asp Lys Gly Glu Ile Val
            115                 120                 125

CAA AAA TAC CGC AAA ATC TTG CCT TGG TGC CCT ATT GAA TGT TGG TAT      432
Gln Lys Tyr Arg Lys Ile Leu Pro Trp Cys Pro Ile Glu Cys Trp Tyr
        130                 135                 140

CCT GGG GAT AAA ACT TAT GTG GTT GAT GGG CCT AAG GGC TTG AAA GTT      480
Pro Gly Asp Lys Thr Tyr Val Val Asp Gly Pro Lys Gly Leu Lys Val
145                 150                 155                 160

TCT TTG ATC ATT TGC GAT GAT GGG AAC TAC CCT GAA ATT TGG CGC GAT      528
Ser Leu Ile Ile Cys Asp Asp Gly Asn Tyr Pro Glu Ile Trp Arg Asp
                165                 170                 175

TGC GCG ATG CGT GGG GCA GAA CTC ATT GTG CGC TGT CAA GGT TAC ATG      576
Cys Ala Met Arg Gly Ala Glu Leu Ile Val Arg Cys Gln Gly Tyr Met
                180                 185                 190
```

```
TAT CCG GCT AAG GAG CAA CAA ATT GCG ATC GTG AAA GCT ATG GCG TGG        624
Tyr Pro Ala Lys Glu Gln Gln Ile Ala Ile Val Lys Ala Met Ala Trp
        195                 200                 205

GCC AAT CAA TGT TAT GTA GCG GTA GCG AAT GCG ACC GGT TTT GAT GGG        672
Ala Asn Gln Cys Tyr Val Ala Val Ala Asn Ala Thr Gly Phe Asp Gly
    210                 215                 220

GTG TAT TCC TAT TTT GGG CAT TCT AGC ATT ATT GGT TTT GAT GGG CAT        720
Val Tyr Ser Tyr Phe Gly His Ser Ser Ile Ile Gly Phe Asp Gly His
225                 230                 235                 240

ACT TTG GGC GAA TGC GGG GAA GAA GAA AAT GGT CTT CAA TAC GCT CAA        768
Thr Leu Gly Glu Cys Gly Glu Glu Glu Asn Gly Leu Gln Tyr Ala Gln
                245                 250                 255

CTT TCC GTG CAA CAA ATC CGT GAT GCG AGA AAA TAC GAC CAA AGC CAA        816
Leu Ser Val Gln Gln Ile Arg Asp Ala Arg Lys Tyr Asp Gln Ser Gln
            260                 265                 270

AAC CAA CTC TTC AAA CTC TTG CAC AGA GGT TAT AGT GGG GTT TTT GCT        864
Asn Gln Leu Phe Lys Leu Leu His Arg Gly Tyr Ser Gly Val Phe Ala
        275                 280                 285

AGT GGC GAT GGG GAT AAG GGT GTG GCG GAA TGC CCT TTT GAG TTC TAT        912
Ser Gly Asp Gly Asp Lys Gly Val Ala Glu Cys Pro Phe Glu Phe Tyr
    290                 295                 300

AAA ACT TGG GTT AAT GAC CCC AAA AAA GCT CAA GAA AAT GTA GAA AAA        960
Lys Thr Trp Val Asn Asp Pro Lys Lys Ala Gln Glu Asn Val Glu Lys
305                 310                 315                 320

ATC ACT CGC CCA AGC GTG GGT GTG GAC GCT TGT CCT GTG GGC GAT TTG       1008
Ile Thr Arg Pro Ser Val Gly Val Asp Ala Cys Pro Val Gly Asp Leu
                325                 330                 335

CCC ACG AAA TAA                                                        1020
Pro Thr Lys
```

(2) INFORMATION FOR SEQ ID NO:10:

(i) SEQUENCE CHARACTERISTICS:
        (A) LENGTH: 339 amino acids
        (B) TYPE: amino acid
        (D) TOPOLOGY: linear (ii) MOLECULE TYPE: protein (xi) SEQUENCE DESCRIPTION: SEQ ID NO:10:

```
Met Arg His Gly Asp Ile Ser Ser Pro Asp Thr Val Gly Val Ala
 1               5                  10                  15

Val Val Asn Tyr Lys Met Pro Arg Leu His Thr Lys Glu Gln Val Leu
                 20                  25                  30

Glu Asn Cys Arg Asn Ile Ala Lys Val Ile Gly Gly Val Lys Gln Gly
             35                  40                  45

Leu Pro Gly Leu Asp Leu Ile Ile Phe Pro Glu Tyr Ser Thr His Gly
         50                  55                  60

Ile Met Tyr Asp Arg Gln Glu Met Phe Asp Thr Ala Ala Ser Val Pro
 65                  70                  75                  80

Gly Glu Glu Thr Ala Ile Phe Ala Glu Ala Cys Lys Lys Asn Lys Val
                 85                  90                  95

Trp Gly Val Phe Ser Leu Thr Gly Glu Lys His Glu Gln Ala Lys Lys
             100                 105                 110

Asn Pro Tyr Asn Thr Leu Ile Leu Val Asn Asp Lys Gly Glu Ile Val
         115                 120                 125

Gln Lys Tyr Arg Lys Ile Leu Pro Trp Cys Pro Ile Glu Cys Trp Tyr
     130                 135                 140

Pro Gly Asp Lys Thr Tyr Val Val Asp Gly Pro Lys Gly Leu Lys Val
```

```
                    145                 150                 155                 160
Ser Leu Ile Ile Cys Asp Asp Gly Asn Tyr Pro Glu Ile Trp Arg Asp
                165                 170                 175

Cys Ala Met Arg Gly Ala Glu Leu Ile Val Arg Cys Gln Gly Tyr Met
            180                 185                 190

Tyr Pro Ala Lys Glu Gln Gln Ile Ala Ile Val Lys Ala Met Ala Trp
        195                 200                 205

Ala Asn Gln Cys Tyr Val Ala Val Ala Asn Ala Thr Gly Phe Asp Gly
    210                 215                 220

Val Tyr Ser Tyr Phe Gly His Ser Ser Ile Ile Gly Phe Asp Gly His
225                 230                 235                 240

Thr Leu Gly Glu Cys Gly Glu Glu Asn Gly Leu Gln Tyr Ala Gln
                245                 250                 255

Leu Ser Val Gln Gln Ile Arg Asp Ala Arg Lys Tyr Asp Gln Ser Gln
                260                 265                 270

Asn Gln Leu Phe Lys Leu Leu His Arg Gly Tyr Ser Gly Val Phe Ala
            275                 280                 285

Ser Gly Asp Gly Asp Lys Gly Val Ala Glu Cys Pro Phe Glu Phe Tyr
    290                 295                 300

Lys Thr Trp Val Asn Asp Pro Lys Lys Ala Gln Glu Asn Val Glu Lys
305                 310                 315                 320

Ile Thr Arg Pro Ser Val Gly Val Asp Ala Cys Pro Val Gly Asp Leu
                325                 330                 335

Pro Thr Lys (2) INFORMATION FOR SEQ ID NO:11:

(i) SEQUENCE CHARACTERISTICS:
        (A) LENGTH: 345 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

Met Arg His Gly Asp Ile Ser Ser Asn Asp Thr Val Gly Val Ala
1               5                   10                  15

Val Val Asn Tyr Lys Met Pro Arg Leu His Asp Arg Ala Gly Val Leu
                20                  25                  30

Glu Asn Ala Arg Lys Ile Ala Asp Met Met Ile Gly Val Lys Thr Gly
            35                  40                  45

Leu Pro Gly Met Asp Leu Val Val Phe Pro Glu Tyr Ser Thr Gln Gly
        50                  55                  60

Ile Met Tyr Asn Glu Glu Glu Met Tyr Ala Thr Ala Ala Thr Ile Pro
65                  70                  75                  80

Gly Asp Glu Thr Ala Ile Phe Ser Ala Ala Cys Arg Glu Ala Asp Thr
                85                  90                  95

Trp Gly Val Phe Ser Ile Thr Gly Glu Gln His Glu Asp His Pro Asn
            100                 105                 110

Lys Pro Pro Tyr Asn Thr Leu Ile Leu Ile Asp Asn Lys Gly Glu Ile
        115                 120                 125

Val Gln Arg Tyr Arg Lys Ile Leu Pro Trp Cys Pro Ile Glu Gly Trp
    130                 135                 140

Tyr Pro Gly Asp Thr Thr Tyr Val Thr Glu Gly Pro Lys Gly Leu Lys
145                 150                 155                 160
```

```
Ile Ser Leu Ile Ile Cys Asp Asp Gly Asn Tyr Pro Glu Ile Trp Arg
                165                 170                 175

Asp Cys Ala Met Lys Gly Ala Glu Leu Ile Val Arg Cys Gln Gly Tyr
            180                 185                 190

Met Tyr Pro Ala Lys Asp Gln Gln Val Met Met Ser Lys Ala Met Ala
            195                 200                 205

Trp Ala Asn Asn Cys Tyr Val Ala Val Ala Asn Ala Ala Gly Phe Asp
            210                 215                 220

Gly Val Tyr Ser Tyr Phe Gly His Ser Ala Ile Ile Gly Phe Asp Gly
225                 230                 235                 240

Arg Thr Leu Gly Glu Thr Gly Glu Glu Tyr Gly Ile Gln Tyr Ala
                245                 250                 255

Gln Leu Ser Val Ser Ala Ile Arg Asp Ala Arg Glu Asn Asp Gln Ser
                260                 265                 270

Gln Asn His Ile Phe Lys Leu Leu His Arg Gly Tyr Ser Gly Val His
                275                 280                 285

Ala Ala Gly Asp Gly Asp Lys Gly Val Ala Asp Cys Pro Phe Glu Phe
                290                 295                 300

Tyr Lys Leu Trp Val Thr Asp Ala Gln Lys Ala Gln Glu Arg Val Glu
305                 310                 315                 320

Ala Ile Thr Arg Asp Thr Val Gly Val Ala Asp Cys Arg Val Gly Asn
                325                 330                 335

Leu Pro Val Glu Lys Thr Val Glu Ala
                340                 345

(2) INFORMATION FOR SEQ ID NO:12:

(i) SEQUENCE CHARACTERISTICS:
        (A) LENGTH: 346 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Met Arg His Gly Asp Ile Ser Ser Asn Asp Thr Val Gly Val Ala
1               5                   10                  15

Val Val Asn Tyr Lys Met Pro Arg Leu His Thr Ala Ala Glu Val Leu
                20                  25                  30

Asp Asn Ala Arg Lys Ile Ala Asp Met Ile Val Gly Met Lys Gln Gly
            35                  40                  45

Leu Pro Gly Met Asp Leu Val Val Phe Pro Glu Tyr Ser Leu Gln Gly
            50                  55                  60

Ile Met Tyr Asp Pro Ala Glu Met Met Glu Thr Ala Val Ala Ile Pro
65                  70                  75                  80

Gly Glu Glu Thr Glu Ile Phe Ser Arg Ala Cys Arg Lys Ala Asn Val
                85                  90                  95

Trp Gly Val Phe Ser Leu Thr Gly Glu Arg His Glu Glu His Pro Arg
                100                 105                 110

Lys Ala Pro Tyr Asn Thr Leu Ile Leu Ile Asp Asn Asn Gly Glu Ile
            115                 120                 125

Val Gln Lys Tyr Arg Lys Ile Ile Pro Trp Cys Pro Ile Glu Gly Trp
            130                 135                 140

Tyr Pro Gly Gly Gln Thr Tyr Val Ser Glu Gly Pro Lys Gly Met Lys
145                 150                 155                 160
```

```
Ile Ser Leu Ile Ile Cys Asp Asp Gly Asn Tyr Pro Glu Ile Trp Arg
            165                 170                 175
Asp Cys Ala Met Lys Gly Ala Glu Leu Ile Val Arg Cys Gln Gly Tyr
            180                 185                 190
Met Tyr Pro Ala Lys Asp Gln Gln Val Met Met Ala Lys Ala Met Ala
            195                 200                 205
Trp Ala Asn Asn Cys Tyr Val Ala Val Ala Asn Ala Ala Gly Phe Asp
            210                 215                 220
Gly Val Tyr Ser Tyr Phe Gly His Ser Ala Ile Ile Gly Phe Asp Gly
225                 230                 235                 240
Arg Thr Leu Gly Glu Cys Gly Glu Glu Met Gly Ile Gln Tyr Ala
            245                 250                 255
Gln Leu Ser Leu Ser Gln Ile Arg Asp Ala Arg Ala Asn Asp Gln Ser
            260                 265                 270
Gln Asn His Leu Phe Lys Leu Leu His Arg Gly Tyr Ser Gly Leu Gln
            275                 280                 285
Ala Ser Gly Asp Gly Asp Arg Gly Leu Ala Glu Cys Pro Phe Glu Phe
            290                 295                 300
Tyr Arg Thr Trp Val Thr Asp Ala Glu Lys Ala Arg Asp Asn Val Glu
305                 310                 315                 320
Arg Leu Thr Arg Ser Thr Thr Gly Val Ala Gln Cys Pro Val Gly Arg
            325                 330                 335
Leu Pro Tyr Glu Gly Leu Glu Lys Glu Ala
            340                 345

(2) INFORMATION FOR SEQ ID NO:13:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..288

(xi) SEQUENCE DESCRIPTION: SEQ ID NO:13:

ATG CCT GCA GGT CGA GCG CTC ATT AAA AAA GGC GTT GTT TTT GAT GAA      48
Met Pro Ala Gly Arg Ala Leu Ile Lys Lys Gly Val Val Phe Asp Glu
  1               5                  10                  15

ATC TTT TAT AAC CAG GAT TTG GAA CTC ACT GAG GGC GCT AGG AGC AAT      96
Ile Phe Tyr Asn Gln Asp Leu Glu Leu Thr Glu Gly Ala Arg Ser Asn
             20                  25                  30

CTT GTT TTA GAA ATC CAT AAC AGG CTT TTA ACC CCT TAT TTT AGC GCG     144
Leu Val Leu Glu Ile His Asn Arg Leu Leu Thr Pro Tyr Phe Ser Ala
         35                  40                  45

GGC GCG TTA AAC GGG ACG GGT GTT GTG GGG TTG TTA AAA AAG GGT CTT     192
Gly Ala Leu Asn Gly Thr Gly Val Val Gly Leu Leu Lys Lys Gly Leu
     50                  55                  60

GTT GGG CAT GCC CCT TTG AAA TTG CAA GAC TTG CAA AGA GCG GCT AAA     240
Val Gly His Ala Pro Leu Lys Leu Gln Asp Leu Gln Arg Ala Ala Lys
 65                  70                  75                  80

ATC TAT TGC ATT AAC GCG CTA TAT GGC TTA GTG GAA GTG AAA ATC AAA     288
Ile Tyr Cys Ile Asn Ala Leu Tyr Gly Leu Val Glu Val Lys Ile Lys
                 85                  90                  95

TAA                                                                  291
```

(2) INFORMATION FOR SEQ ID NO:14:

(i) SEQUENCE CHARACTERISTICS:
        (A) LENGTH: 96 amino acids
        (B) TYPE: amino acid
        (D) TOPOLOGY: linear (ii) MOLECULE TYPE: protein (xi) SEQUENCE DESCRIPTION: SEQ ID NO:14:

```
Met Pro Ala Gly Arg Ala Leu Ile Lys Lys Gly Val Val Phe Asp Glu
 1               5                  10                  15

Ile Phe Tyr Asn Gln Asp Leu Glu Leu Thr Glu Gly Ala Arg Ser Asn
             20                  25                  30

Leu Val Leu Glu Ile His Asn Arg Leu Leu Thr Pro Tyr Phe Ser Ala
         35                  40                  45

Gly Ala Leu Asn Gly Thr Gly Val Val Gly Leu Leu Lys Lys Gly Leu
     50                  55                  60

Val Gly His Ala Pro Leu Lys Leu Gln Asp Leu Gln Arg Ala Ala Lys
 65                  70                  75                  80

Ile Tyr Cys Ile Asn Ala Leu Tyr Gly Leu Val Glu Val Lys Ile Lys
                 85                  90                  95
```

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate primer"

(xi) SEQUENCE DESCRIPTION: SEQ ID NO:15:

CCTTATAACA CTTTGATTCT TGTC                                                24

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "degenerate primer"

(xi) SEQUENCE DESCRIPTION: SEQ ID NO:16:

CAAGCCCTTA GGCCCATCAA CC                                                  22

We claim:

1. A process of screening for a compound capable of inhibiting the amidase activity of a *Helicobacter amidase*, comprising contacting the compound with a *Helicobacter aliphatic* amidase, and selecting the compound that inhibits the amidase activity of the Helicobacter aliphatic amidase wherein the Helicobacter aliphatic amidase is an AimE polypeptide.

2. A process of screening for a compound capable of inhibiting the amidase activity of a *Helicobacter amidase*, comprising contacting the compound with a Helicobacter aliphatic amidase, wherein the Helicobacter aliphatic amidase has an amino acid sequence comprising SEQ ID NO:10, and selecting the compound that inhibits the amidase activity of the Helicobacter aliphatic amidase.

\* \* \* \* \*